(12) United States Patent
Ekström et al.

(10) Patent No.: US 10,322,087 B2
(45) Date of Patent: Jun. 18, 2019

(54) TARGETED LIPOSOMAL DELIVERY OF CGMP ANALOGUES

(71) Applicant: Mireca Medicines GmbH, Tubingen (DE)

(72) Inventors: Per Ekström, Lund (SE); François Paquet-Durand, Tübingen (DE); Pieter Jaap Gaillard, Leiden (NL); Valeria Marigo, Modena (IT); Hans-Gottfried Genieser, Lemwerder (DE); Andreas Rentsch, Bremen (DE); Dragana Trifunovic, Tübingen (DE); Ayse Sahaboglu Tekgoz, Tübingen (DE)

(73) Assignee: Mireca Medicines GmbH, Tübingen (DE)

(*) Notice: Subject to any disclaimer, the term of this patent is extended or adjusted under 35 U.S.C. 154(b) by 0 days.

(21) Appl. No.: 15/558,637

(22) PCT Filed: Mar. 16, 2016

(86) PCT No.: PCT/EP2016/055659
§ 371 (c)(1),
(2) Date: Sep. 15, 2017

(87) PCT Pub. No.: WO2016/146669
PCT Pub. Date: Sep. 22, 2016

(65) Prior Publication Data
US 2018/0085311 A1    Mar. 29, 2018

(30) Foreign Application Priority Data
Mar. 16, 2015 (EP) .................................. 15159285

(51) Int. Cl.
*A61K 9/127* (2006.01)
*A61K 9/00* (2006.01)
*A61K 31/708* (2006.01)

(52) U.S. Cl.
CPC .......... *A61K 9/1271* (2013.01); *A61K 9/0019* (2013.01); *A61K 9/0048* (2013.01);
(Continued)

(58) Field of Classification Search
None
See application file for complete search history.

(56) References Cited

U.S. PATENT DOCUMENTS 5,625,056 A * 4/1997 Genieser ............... C07H 19/20
                                                          536/26.12
8,524,274 B2    9/2013 Wagner et al.
(Continued)

FOREIGN PATENT DOCUMENTS

EP            0825852 B1 *   7/2004   ........... A61K 9/1278
WO    WO-03/007979 A1        1/2003
WO    WO-2010/095940 A2      8/2010

OTHER PUBLICATIONS

V Guadagni, E Novelli, I Piano, C Gargini, E Strettoi. "Pharmacological approaches to retinitis pigmentosa: A laboratory perspective." Progress in Retinal and Eye Research, vol. 48, 2015, pp. 62-81. (Year: 2015).*

(Continued)

*Primary Examiner* — Isaac Shomer
(74) *Attorney, Agent, or Firm* — Gilberto M. Villacorta; Sunit Talapatra; Foley & Lardner LLP

(57) ABSTRACT

The invention relates to means and methods of targeted drug delivery of therapeutic agent to and across the blood-ocular barrier. In particular, the invention relates to cyclic guanosine-3', 5'-monophosphate analogs as therapeutic agent for treating retinal diseases. The cGMPSs targeted to the blood-ocular barrier by glutathione-based ligands that facilitate the specific binding to and enhanced internalization by glutathione transporters present on the blood-ocular barrier. The (Continued)

glutathione-based ligands are conjugated to nanocontainers such as liposomes encapsulating the cGMPSs.

17 Claims, 10 Drawing Sheets

(52) U.S. Cl.
CPC ............ *A61K 31/708* (2013.01); *Y02A 50/411* (2018.01); *Y02A 50/414* (2018.01); *Y02A 50/422* (2018.01); *Y10S 977/773* (2013.01); *Y10S 977/906* (2013.01); *Y10S 977/907* (2013.01)

(56) References Cited

U.S. PATENT DOCUMENTS

| | | | | |
|---|---|---|---|---|
| 2007/0184044 | A1* | 8/2007 | Dawson-Scully | A61K 38/08 424/94.5 |
| 2009/0124558 | A1* | 5/2009 | Dawson-Scully | A61K 31/351 514/6.9 |
| 2011/0305751 | A1* | 12/2011 | Gaillard | A61K 49/0002 424/450 |
| 2013/0324592 | A1* | 12/2013 | Rodriguez Gascon | A61K 9/0048 514/44 A |

OTHER PUBLICATIONS

EJ Tsai, DA Kass. "Cyclic GMP signaling in cardiovascular pathophysiology and therapeutics." Pharmacology & Therapeutics, vol. 122, 2009, pp. 216-238. (Year: 2009).*

N Valtcheva, P Nestorov, A Beck, M Russwurm, M Hillenbarnd, P Weinmeister, R Feil. "The Commonly Used cGMP-dependent Protein Kinase Type I (cGKI) Inhibitor Rp-8-Br-PET-cGMPS Can Activate cGKI in Vitro and in Intact Cells." Journal of Biological Chemistry, vol. 284, No. 1, 2009, pp. 556-562. (Year: 2009).*

AM Northover, BJ Northover. "Some Cyclic Nucleotides Reduce Phenylephrine-Induced and Phorbol Ester-Induced Constriction of the Rat Anterior Mesenteric Artery." General Pharmacology, vol. 28 No. 1, 1997, pp. 139-143. (Year: 1997).*

A Szmidt-Jaworska, K Jaworski, J Kopcewicz. "Cyclic GMP stimulates flower induction of Pharbitis nil via its influence on cGMP regulated protein kinase." Plant Growth and Regulation, vol. 57, 2009, pp. 115-126. (Year: 2009).*

BJ Gjersten, G Mellgren, A Otten, A Maronde, H-G Genieser, B Jastorff, OK Vintermyr, GS McKnight, SO Doskeland. "Novel (Rp)-cAMPS Analogs as Toos for Inhibition of cAMP-Kinase in Cell Culture." The Journal of Biological Chemistry, vol. 270 No. 35, 1995, pp. 20599-20607. (Year: 1995).*

P Weinmeister, R Lukowski, S Linder, W Erl, R Brandl, S Feil, F Hofmann, R Feil. "Regulation of vascular smooth muscle growth by cyclic nucleotides and cGMP-dependent protein kinase." BioMed Central Pharmacology, 2005, 5(Suppl 1):P62, 1 printed page. (Year: 2005).*

F Paquet-Durand, SM Hauck, T van Veen, M Ueffing, P Ekstrom. "PKG Activity Causes Photoreceptor Cell Death in Two Retinitis Pigmentosa Models." Journal of Neurochemistry, vol. 108, 2009, pp. 796-810. (Year: 2009).*

SM Berge, LD Bighley, DC Monkhouse. "Pharmaceutical Salts." Journal of Pharmaceutical Sciences, vol. 66 No. 1, Jan. 1977, pp. 1-19. (Year: 1977).*

Anonymous: "Drugs for retinal degeneration", Oct. 25, 2014, XP002741507, retrieved from the Internet on Jun. 25, 2015: URL:https://web.archive.org/web/20141025231945/http://www.drugsford.eu/, 2 pgs.

Finley et al., "Effects of cyclic amp-containing lipid vesicles on dictyostelium discoideum aggregation", Biochimica et Biophysica Acta., 1983, vol. 755, pp. 1-9.

Reijerkerk et al., "Systemic treatment with gluthione PEGylated liposomal methyloprednisolone (2B3-201) improves therapeutic efficacy in a model of ocular inflammation", Investigative Ophthalmology & Visual Science, 2014, vol. 55, pp. 2788-2794.

Thrimawithana et al., "Drug delivery to the posterior segment of the eye", Drug Discovery Today, Mar. 2011, vol. 16, No. 5/6, pp. 270-277.

Valtcheva et al., "The commonly used cGMP-dependent protein kinase Type I (cGKI) inhibitor Rp-8-Br-PET-cGMPS can activate cGKI in vitra and in intact cells", The Journal of Biological Chemistry, Jan. 2, 2009, vol. 284, No. 1, pp. 556-562.

International Search Report issued in International Patent Application No. PCT/EP2016/055659, dated Feb. 5, 2016.

* cited by examiner

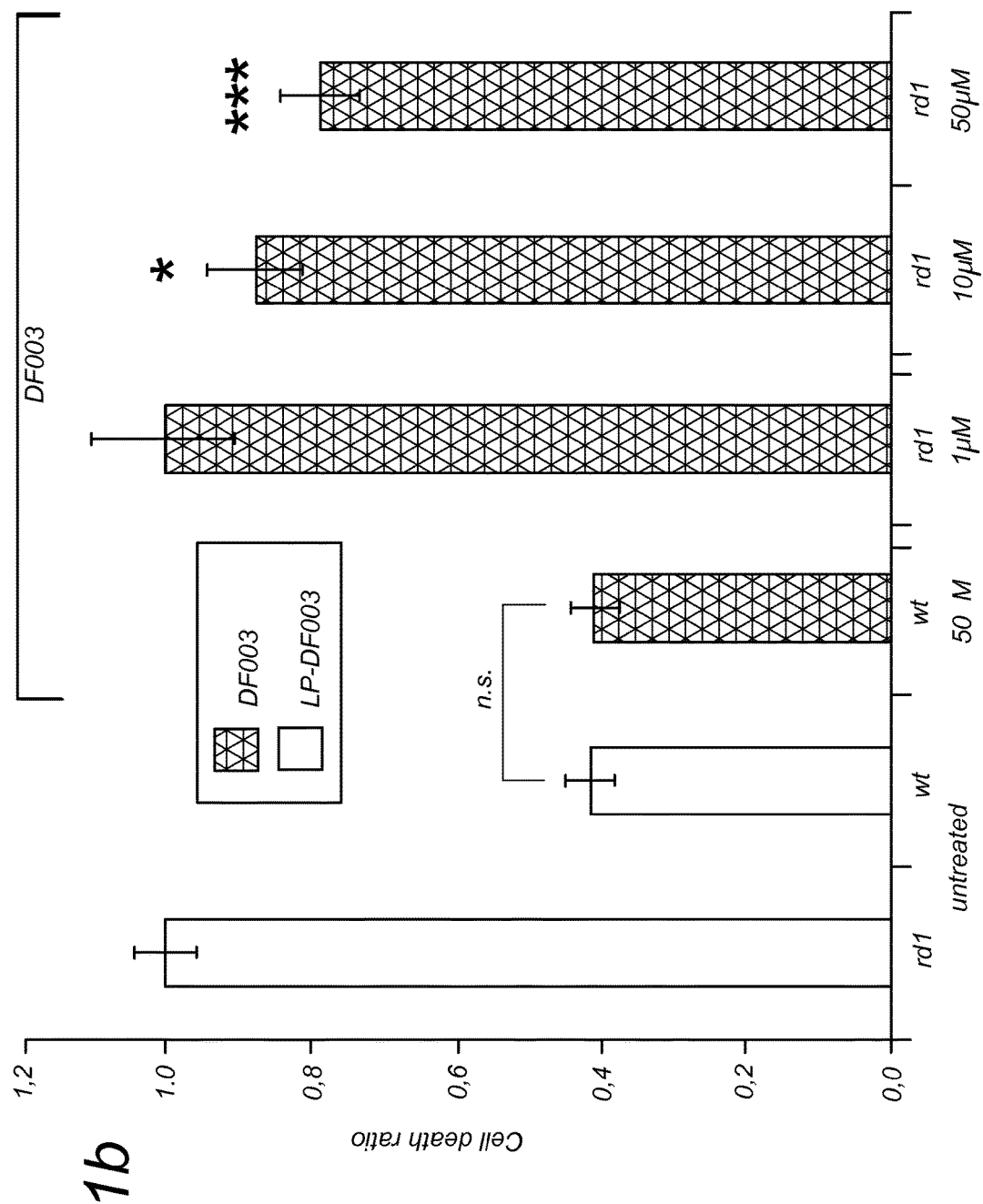

TARGETED LIPOSOMAL DELIVERY OF CGMP ANALOGUES

CROSS-REFERENCE TO RELATED APPLICATIONS

This application is the National Phase of International Patent Application No. PCT/EP2016/055659, filed Mar. 16, 2016, published on Sep. 22, 2016 as WO 2016/146669 A1, which claims priority to European Patent Application No. 15159285.4, filed Mar. 16, 2015. The contents of these applications are herein incorporated by reference in their entirety.

FIELD OF THE INVENTION

The present invention relates to the fields of medicine and pharmacy. In particular the invention relates to the field of targeted drug delivery. The invention relates to conjugates of active pharmaceutical ingredients, comprised in nanocontainers, optionally linked with ligands for glutathione transporters that specifically mediate enhanced binding, endo- or transcytosis to and across the blood-ocular barrier. These conjugates are preferably used in methods for treatment or prevention of diseases of the retina.

BACKGROUND OF THE INVENTION

Retinitis pigmentosa (RP) is a group of severely disabling inherited neurodegenerative diseases. Typically, rod photoreceptor cells—permitting vision under dim light conditions—degenerate first during the course of the disease. Subsequently, the loss of rods triggers a secondary degeneration of cone photoreceptor cells, the source of high-resolution colour vision in daylight, eventually leading to complete blindness.

Retinitis pigmentosa is caused by a wide and disparate set of mutations, currently identified in over 70 genes (cf. retinal information network: https://sph.uth.edu/retnet). Although many of the causative mutations have been defined, there is still only very little information on the subsequent degeneration mechanisms. The details that we know so far have mostly come from studies on animal models (usually rodent based), that display gene mutations homologous to human retinitis pigmentosa patient cohorts.

The genes mutated in retinitis pigmentosa are usually associated with photoreceptor function, but there are also such that relate to general cellular functions (Kennan et al. 2005, Trends Genet. 21, 103-110). The molecule cGMP (cyclic guanosine-monophosphate) plays a direct role in the phototransduction cascade, which takes place within the photoreceptor cells when these are hit by light. In many cases, retinitis pigmentosa mutations lead to an excessive accumulation of cGMP in photoreceptors (Arango-Gonzalez et al. 2014 PLoS One. 9, e112142), for instance in situations where genes for enzymes involved in photoreceptor cGMP metabolism are affected. This is the case for mutations in phosphodiesterase 6 (whose subunits are encoded by genes PDE6B, PDE6A, PDE6G and PDE6C, PDE6H for cone photoreceptors) the photoreceptor enzymes that hydrolyse cGMP to GMP. The Pde6b gene is mutated in the rd1 mouse model of retinitis pigmentosa, which has been well studied in many laboratories. In a supposed chain of events, the accumulation of cGMP in PDE6B mutant retina occurs as a direct consequence of the actual gene defect, and this may thus be seen as an early and mechanistically fundamental degeneration component. In the next step(s), the increased cGMP can be envisaged to have at least one of four targets: 1) cGMP dependent protein kinase (protein kinase G; PKG), which when activated by cGMP, will phosphorylate specific proteins, 2) cyclic nucleotide gated ion channels (CNGC), which, when activated by cGMP, allow for a cGMP controlled influx of Na$^+$ and Ca$^{2+}$, 3) phosphodiesterase (PDE), and 4) hyperpolarization-activated cyclic nucleotide-gated (HCN) channel. The first two cGMP targets are directly connected with photoreceptor degeneration (Paquet-Durand et al. 2009, J. Neurochem. 108, 796-810; Paquet-Durand et al. 2011, Hum. Mol. Genet. 20, 941-947), while the others are known cGMP targets and hence potentially involved in the degenerative process. Due to their direct connection with the early events, PKG and CNGC can be regarded as disease drivers, even though the downstream mechanisms are still not understood in great detail (Trifunovic et al. 2012, Curr. Mol. Med. 12, 598-612).

There are a variety of experimental treatment approaches for retinitis pigmentosa that are currently being researched and which are at different stages of development, including e.g. gene therapy, stem cell research and optogenetics. However, currently there is no clinically approved treatment available.

Previously, certain cGMP-derived PKG inhibitors, e.g. Rp-8-Br-cGMPS, were found to offer some protection of rd1 and rd2 photoreceptors both in vitro and in in vivo mouse retinitis pigmentosa models (Paquet-Durand et al., 2009). However, these PKG inhibitors would require frequent re-administration (i.e. every other day) of the PKG inhibitor by subtenonal or intravitreal injection, which is not practical for a chronic disease.

There are currently no approved prevention or treatment methods available for retinitis pigmentosa. There is therefore still a need in the art for adequate treatments of retinitis pigmentosa, in particular treatments with a more convenient mode of administration. It is thus an object of the present invention to provide for new means and methods for treating and preventing retinitis pigmentosa.

SUMMARY OF THE INVENTION

In a first aspect, the invention relates to a pharmaceutically acceptable nanocontainer comprising a therapeutic or diagnostic agent for treating or diagnosing a pathology, condition or disorder associated with dysregulation of cGMP-effected cellular target, wherein preferably the target is at least one of a cGMP-dependent protein kinase (PKG), a hyperpolarization-activated cyclic nucleotide-gated (HCN) channel, a phosphodiesterase (PDE) and a cGMP-gated channel (CNGC). Preferably, the nanocontainer is conjugated to a ligand for a glutathione transporter. In a nanocontainer according to the invention, the therapeutic agent preferably is a cyclic guanosine-3', 5'-monophosphate analogue, more preferably an analogue of the formula I:

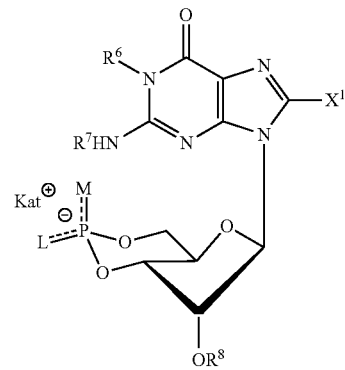

wherein both $R^6$ and $R^7$ are hydrogen, while $X^1$ is —$CF_3$ or a —$NR^9R^{10}$ or —$SR^{11}$ group, wherein $R^9$ is hydrogen and both $R^{10}$ and $R^{11}$ are alkyl groups with a terminal $NH_2$ or OH group, or $R^{11}$ is a phenyl group

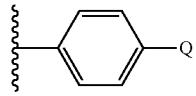

having in the 4-position a substituent Q as depicted wherein Q is —F, —Cl, —Br, —I, —OH, —SH, $NH_2$, $NO_2$, —$OCH_3$, $CH_3$ or $CF_3$, or $R^9$ and $R^{10}$ both are alkyl groups which are connected to each other to form a ring, $R^8$ is hydrogen, a (tri)alkylsilyl group or an acyl group, and wherein L is oxygen, sulphur, borano ($BH_3$) or a further substituted borano group, and M is OH, or L is OH, and M is oxygen, sulphur, borano ($BH_3$) or a further substituted borano group, and $Kat^+$ is a proton or another physiologically acceptable metal cation or a trialkylammonium ion, or $R^6$ and $R^7$ together are a styrylene group and form a condensed tricyclic ring system according to formula II:

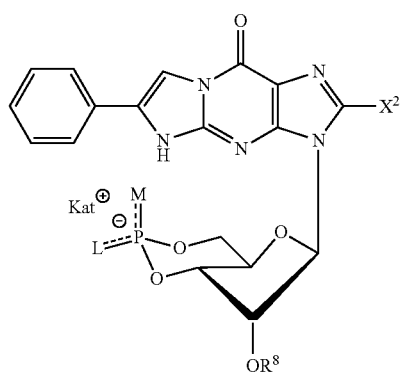

wherein $X^2$ is hydrogen, —F, —Cl, —Br, —I, $CF_3$ or a —$NR^9R^{10}$ or —$SR^{11}$ group, or a 4-chlorophenylthio group, wherein $R^9$ is hydrogen and both $R^{10}$ and $R^{11}$ are alkyl groups with a terminal $NH_2$ or OH group, $R^8$ is hydrogen, a (tri)alkylsilyl group or an acyl group, and wherein L is oxygen, sulphur, borano (BH3) or a further substituted borano group, and M is OH, or L is OH, and M is oxygen, sulphur, borano (BH3) or a further substituted borano group, and $Kat^+$ is a proton or another physiologically acceptable metal cation or a trialkylammonium ion.

Particularly preferred are cyclic guanosine-3', 5'-monophosphate analogues of the formula III:

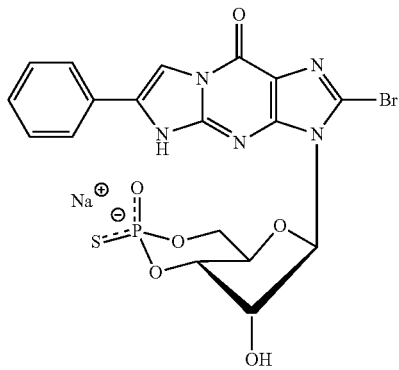

or of the formula IV:

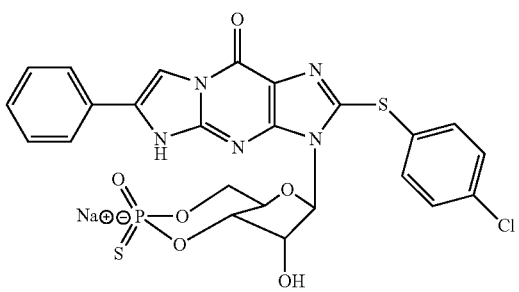 [SMILES: O=c1c2nc(Sc3ccc(Cl)cc3)n(C3OC4CO[P-](=O)(=S)OC4C3O)c2nc2[nH]c(-c3ccccc3)cn12 ; [Na+]]

or other pharmaceutically acceptable salts of the analogues of formulas III and IV than their sodium salts.

In a nanocontainer according to the invention, the ligand for a glutathione transporter preferably is a ligand selected from the group consisting of: glutathione, S-(p-bromobenzyl)glutathione, gamma-(L-gamma-azaglutamyl)-S-(p-bromobenzyl)-L-cysteinylglycin, S-butylglutathione, S-decylglutathione, glutathione reduced ethyl ester, glutathionesulfonic acid, S-hexylglutathione, S-lactoylglutathione, S-methylglutathione, S-(4-nitrobenzyl)glutathione, S-octylglutathione, S-propylglutathione, n-butanoyl gamma-glutamylcysteinylglycine, ethanoyl gamma-glutamylcysteinylglycine, hexanoyl gamma-glutamylcysteinylglycine, octanoyl gamma-glutamylcysteinylglycine, dodecanoyl gamma-glutamylcysteinylglycine, GSH monoisopropyl ester (N—(N-L-glutamyl-L-cysteinyl)glycine 1-isopropyl ester sulfate monohydrate) and glutathione derivatives of the formula V:

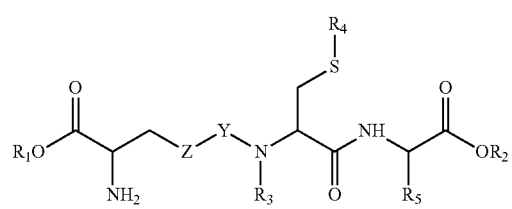

wherein Z=$CH_2$ and Y=$CH_2$, or Z=O and Y=C=O;
$R_1$ and $R_2$ are independently selected from the group consisting of H, linear or branched alkyl (1-25C), aralkyl (6-26C), cycloalkyl (6-25C), heterocycles (6-20C), ethers or polyethers (3-25C), and where $R_1$-$R_2$ together have 2-20C atoms and form a macrocycle with the remainder of formula VI;

$R_3$ is selected from the group consisting of H and $CH_3$;

$R_4$ is selected form the group consisting of 6-8C alkyl, benzyl, naphthyl and a therapeutically active cyclic guanosine-3', 5'-monophosphorothioate; and, $R_5$ is selected from the group consisting of H, phenyl, $CH_3$- and $CH_2$-phenyl; or, a pharmaceutically acceptable salt thereof, and wherein preferably in the derivative of formula I $R_3$ is H, $R_4$ is benzyl, and $R_5$ is phenyl.

A preferred nanocontainer according to the invention is a liposome encapsulating the therapeutic or diagnostic agent, wherein preferably the ligand for a glutathione transporter is conjugated to the liposome through a bifunctional conjugation agent comprising a vitamin E derivative or a phospholipid bonded to one end of the conjugation agent and the ligand for a glutathione transporter bonded to the other end of the conjugation agent, wherein more preferably, the conjugation agent is polyethylene glycol having polymerization number (n) of between about 6-210, and wherein most preferably the polyethylene glycol has a molecular weight between 1,000 and 5,000 Da. Particularly preferred is a conjugation agent that is obtainable by reacting distearoylphosphatidylethanolamine-polyethylene glycol-maleimide (DSPE-PEG-MAL) with a ligand for a glutathione receptor having a maleimide-reactive thiol group and wherein preferably the DSPE-PEG-MAL has a molecular weight of around 2,000 Da. A preferred ligand for a glutathione receptor is glutathione.

In a second aspect, the invention pertains to a pharmaceutical composition comprising a nanocontainer according to the invention and pharmaceutically acceptable carrier.

In a third aspect, the invention pertains to a nanocontainer according to the invention, or a pharmaceutical composition comprising such nanocontainer, for use as a medicament.

In a fourth aspect, the invention pertains to a nanocontainer according to the invention, or a pharmaceutical composition comprising such nanocontainer, for use in the treatment of a pathology, condition or disorder associated with dysregulation of cGMP-effected cellular target, wherein preferably the target is at least one of a cGMP-dependent protein kinase (PKG), a hyperpolarization-activated cyclic nucleotide-gated (HCN) channel, a phosphodiesterase (PDE) and a cGMP-gated channel. Preferably, the nanocontainer or composition is used in the treatment of at least one of: a) retinitis pigmentosa or another a hereditary disease of the retina; b) secondary pigmentary retinal degeneration as a results of a metabolic or neurodegenerative disease, a syndrome or an eye disease; c) diseases of the retina comprising diabetic retinopathy, age related macular degeneration, macular Hole/Pucker, ocular malignancies, retinoblastoma, retinal detachment and river blindness; and, d) neuronal or neurodegenerative disorders, anosmia, inflammatory and neuropathic pain, axonal regrowth and recovery after spinal cord injury e) parasitic diseases such as malaria, African trypanosomiasis, and Chagas disease; and, cardiovascular diseases, hypertension, hypotension, angina pectoris, pulmonary hypertension, erectile dysfunction, ischemic stroke, atherosclerosis, cancer, or acute shock.

Preferably, the nanocontainer or the pharmaceutical composition comprising the nanocontainer for a use as a medicament or for a use as a treatment according to the invention is administered systemically or locally, wherein preferably the nanocontainer or the pharmaceutical composition comprising the nanocontainer is administered by at least one of a) injection or infusion by at least one of intravitreal, intravenous, intraperitoneal, and intraarterial route, and b) topical or ocular application.

Preferably, a treatment according to the invention comprises systemic or local administration of the nanocontainer or the pharmaceutical composition comprising the nanocontainer, wherein preferably, the administration is by at least one of a) injection or infusion by at least one of intravitreal, intravenous, intraperitoneal and intraarterial routes, and b) topical or ocular application.

The nanocontainer preferably is administered in doses of between 0.1 and 1000 mg/kg once per 1 or 2 days. Alternatively, for ocular diseases, nanocontainers can be intravitreally injected, with or without a targeting ligand conjugated thereto, once per two weeks or once per six weeks.

DESCRIPTION OF THE INVENTION

In a first aspect, the invention relates to nanocontainers for targeting therapeutically active and/or diagnostic agents to and across the blood-ocular barrier. Preferably the nanocontainers of the invention comprise a therapeutic or diagnostic agent for treating or diagnosing a pathology, condition or disorder associated with dysregulation of a cGMP-effected cellular target, wherein preferably the target is at least one of a cGMP-dependent protein kinase (PKG) a hyperpolarization-activated cyclic nucleotide-gated (HCN) channel, a phosphodiesterase (PDE) and a cGMP-gated channel (CNGC). The therapeutic or diagnostic agent can be a small organic molecule, a protein, e.g. a enzyme or an antibody, or a nucleic acid such as e.g. a gene therapy vector. A preferred therapeutic agent to be comprised in a nanocontainer according to the invention is a cyclic guanosine-3', 5'-monophosphate analogue.

In a preferred embodiment, a nanocontainer according to the invention is conjugated to a ligand for a glutathione transporter.

A "conjugate" is herein defined as consisting of two entities that are coupled together.

Preferably, the two entities are conjugated by non-specific or specific protein-protein interaction, by covalent bonding, by non-covalent bonding, by coordinating chemical bonding and/or by hydrophobic interactions. In the context of the present invention the first entity may be a pharmaceutically acceptable carrier comprising a therapeutic or diagnostic agent as herein defined below, whereas the second entity will usually be a ligand for a receptor on a target cell as herein defined below.

Cyclic Guanosine-3', 5'-Monophosphate Analogues

The cyclic guanosine-3', 5'-monophosphate (cGMP) analogues that are comprised in the nanocontainers of the invention preferably are of the formula I:

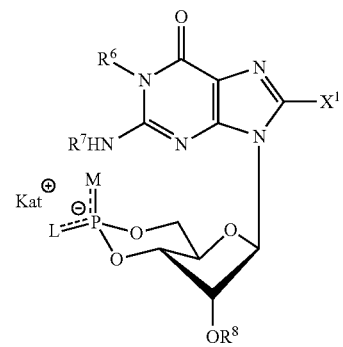

Both $R^6$ and $R^7$ are hydrogen, while $X^1$ is —$CF_3$ or a —$NR^9R^{10}$ or —$SR^{11}$ group, wherein $R^9$ is hydrogen and both $R^{10}$ and $R^{11}$ are alkyl groups with a terminal $NH_2$ or OH group, or $R^{11}$ is a phenyl group

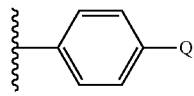

having in the 4-position a substituent Q as depicted
wherein
Q is —F, —Cl, —Br, —I, —OH, —SH, $NH_2$, $NO_2$, —$OCH_3$, $CH_3$ or $CF_3$, or $R^9$ and $R^{10}$ both are alkyl groups which are connected to each other to form a ring, $R^8$ is hydrogen, a (tri)alkylsilyl group or an acyl group, and
and wherein
L is oxygen, sulphur, borano ($BH_3$) or a further substituted borano group, and
M is O(H) or
L is O(H), and
M is oxygen, sulphur, borano ($BH_3$) or a further substituted borano group and
$Kat^+$ is a proton or another physiologically acceptable metal cation or a trialkylammonium ion, or
$R^6$ and $R^7$ together are a styrylene group and form a condensed tricyclic ring system according to formula II:

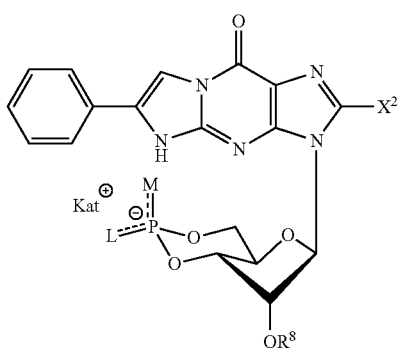

wherein
$X^2$ is hydrogen, —F, —Cl, —Br, —I, $CF_3$ or a —$NR^9R^{10}$ or —$SR^{11}$ group, or a 4-chlorophenylthio group, wherein $R^9$ is hydrogen and both $R^{10}$ and $R^{11}$ are alkyl groups with a terminal $NH_2$ or OH group,
$R^8$ is hydrogen, a (tri)alkylsilyl group or an acyl group, and wherein
L is oxygen, sulphur, borano (BH3) or a further substituted borano group, and
M is O(H), or
L is O(H), and
M is oxygen, sulphur, borano (BH3) or a further substituted borano group, and
$Kat^+$ is a proton or another physiologically acceptable metal cation or a trialkylammonium ion.
Cyclic guanosine-3', 5'-monophosphate compounds according to formula I having hydrophobic aromatic substituents in position 8 are preferred. Especially preferred are compounds substituted in position 8 by phenylthio groups, e.g. 4-chlorophenylthio- or 4-hydroxyphenylthio groups.

Preferred as well are structures according to formula II, which carry halogens or a 4-chlorophenythio group in position 8 of the nucleobase.
Preferred metal cations are $Na^+$, $K^+$, $Ca^{2+}$ and $Mg^{2+}$.
Cyclic guanosine-3', 5'-monophosphate compounds may further be modified as described in U.S. Pat. No. 5,625,056.
Also, the cyclic guanosine-3', 5'-monophosphates for the nanocontainers of the invention can be obtained as described in U.S. Pat. No. 5,625,056, WO 2012/130829, Sekhar et al. (1992, Mol. Pharmacol., 42: 103-108) and Miller et al. (1973, Biochemistry 12: 5310-5319).
If the equatorial residue L is sulphur, the corresponding cyclic guanosine-3', 5'-monophosphorothioate compound (cGMPS) is Rp-configurated at phosphorus, if the equatorial residue L is a borano group, the corresponding cyclic guanosine-3', 5'-monoboranophosphate compound (cGMPB) is Sp-configurated at phosphorus.
If the axial residue M is sulphur, the corresponding cyclic guanosine-3', 5'-monophosphorothioate compound is Sp-configurated at phosphorus, if the axial residue M is a borano group, the corresponding cyclic guanosine-3', 5'-monoboranophosphate compound is Rp-configurated at phosphorus.
Cyclic guanosine-3', 5'-monophosphates including Sp-configurated cGMPS compounds and Rp-configurated cGMPB compounds according to the invention are considered to be activators of protein kinase G isozymes as well as of cyclic guanosine-3', 5'-monophosphate-gated ion channels.
Rp-configurated cGMPS compounds and Sp-configurated cGMPB compounds according to the invention are considered to be inhibitors of protein kinase G isozymes and activators of cyclic guanosine-3', 5'-monophosphate-gated ion channels.
According to the invention compounds according to formula II are considered to be inhibitors of cyclic guanosine-3', 5'-monophosphate-gated ion channels.
According to the invention Sp-configurated cGMPS compounds according to formula II and Rp-configurated cGMPB compounds according to formula II are considered to be activators of protein kinase G isozymes while being inhibitors of cyclic guanosine-3', 5'-monophosphate-gated ion channels.
According to the invention Rp-configurated cGMPS compounds according to formula II and Sp-configurated cGMPB compounds according to formula II are considered to be inhibitors of both, protein kinase G isozymes and cyclic guanosine-3', 5'-monophosphate-gated ion channels.
In a preferred nanocontainer of the invention, the cyclic guanosine-3', 5'-monophosphorothioate is Rp-configurated and of the formula III:

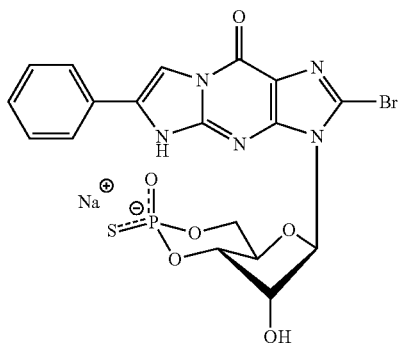

wherein the sodium cation can be any other pharmaceutically acceptable cation, e.g. a proton or another physiologically acceptable metal cation or a trialkylammonium ion. Formula III also exemplifies a compound with a "β-phenyl-1, N²-etheno" (PET) modification.

This preferred cyclic guanosine-3', 5'-monophosphorothioate is also referred to abbreviated scientific name as Rp-8-Br-PET-cGMPS or as DF003 in the Examples herein. Its full scientific name, computed according to the IUPAC nomenclature, is: Sodium, 3-[(4 aR,6R,7R,7aS)-7-hydroxy-2-oxido-2-sulfanylidene-4a,6,7,7a-tetrahydro-4H-furo [3,2-d] [1,3,2] dioxaphosphinin-6-yl]-2-bromo-6-phenyl-5H-imidazo [1,2-a] purin-9-one. Rp-8-Br-PET-cGMPS is commercially available from BIOLOG Life Science Institute GmbH, Bremen, Germany (Cat. No.: P 007 CAS No.: [172806-20-1]). In a preferred embodiment wherein Rp-8-Br-PET-cGMPS is encapsulated into liposomes by remote loading, $Ca^{2+}$ is most preferred as counter cation in the interior of the liposome (see below).

In another preferred nanocontainer of the invention, the cyclic guanosine-3', 5'-monophosphorothioate is Rp-configurated and of the formula IV:

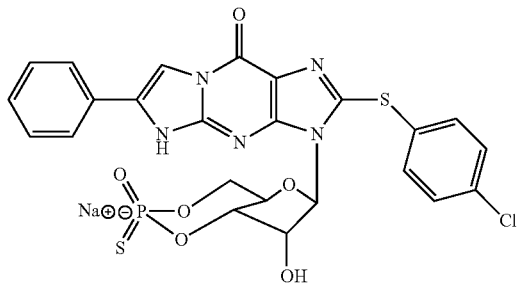 [SMILES: O=c1c2nc(Sc3ccc(Cl)cc3)n(C3OC4CO[P-](=O)(=S)OC4C3O)c2nc2[nH]c(-c3ccccc3)cn12 ; [Na+]]

This preferred cyclic guanosine-3', 5'-monophosphorothioate is also referred to abbreviated scientific name as Rp-8-pCPT-PET-cGMPS. Rp-8-pCPT-PET-cGMPS is commercially available from BIOLOG Life Science Institute GmbH, Bremen, Germany (Cat. No.: C 046, CAS No.: [1262749-62-1]).

According to the invention, the nanocontainers are loaded with cyclic guanosine-3', 5'-monophosphate compounds.

The selection of a compound from the preferred embodiments is governed by the target binding protein(s) that shall be modulated:

If the activation of a cyclic guanosine-3', 5'-monophosphate dependent protein kinase is the task, according to the invention, the preferred loading of the nanocontainer is a cGMP compound without any modification at phosphorus or a Sp-configurated cGMPS compound or a Rp-configurated cGMPB compound.

If the inhibition of a cyclic guanosine-3', 5'-monophosphate dependent protein kinase is the biological task, according to the invention the preferred loading of the nanocontainer is a Rp-configurated cGMPS compound or a Sp-configurated cGMPB compound.

If the activation of a cyclic guanosine-3', 5'-monophosphate gated ion channel is the task, according to the invention, the preferred loading of the nanocontainer is a cGMP compound or a cGMPS compound or a cGMPB compound without any PET-modification.

If the simultaneous activation of a cyclic guanosine-3', 5'-monophosphate dependent protein kinase and a cyclic guanosine-3', 5'-monophosphate gated ion channel is the task, according to the invention, the preferred loading of the nanocontainer is a cGMP compound or a Sp-configurated cGMPS compound or a Rp-configurated cGMPB compound without any PET-modification.

If the simultaneous inhibition of a cyclic guanosine-3', 5'-monophosphate dependent protein kinase and a cyclic guanosine-3', 5'-monophosphate gated ion channel is the task, according to the invention, the preferred loading of the nanocontainer is a Rp-configurated cGMPS compound with PET modification or a Sp-configurated cGMPB compound with PET modification.

Further examples of activating cyclic guanosine-3', 5'-monophosphate analogues include 8-Bromoguanosine-3', 5'-cyclic monophosphate (8-Br-cGMP), 8-(2, 4-Dihydroxyphenylthio)guanosine-3', 5'-cyclic monophosphate (8-o, pDHPT-cGMP), 8-(2-Aminophenylthio)guanosine-3', 5'-monophosphate (8-APT-cGMP), 8-(4-Hydroxyphenylthio)guanosine-3', 5'-cyclic monophosphate (8-pHPT-cGMP), 8-(4-Aminophenylthio)guanosine-3', 5'-monophosphate (8-pAPT-cGMP), 8-(4-Chlorophenylthio)-β-phenyl-1, N²-ethenoguanosine-3', 5'-cyclic monophosphate (8-pCPT-PET-cGMP), 8-(4-Chlorophenylthio)guanosine-3', 5'-cyclic monophosphate (8-pCPT-cGMP), 8-(2, 4-Dichlorophenylthio)guanosine-3', 5'-cyclic monophosphate (8-o,pDClPT-cGMP), 8-(4-Methoxyphenylthio)guanosine-3', 5'-cyclic monophosphate (8-pMeOPT-cGMP), 8-Bromo-β-phenyl-1, N²-ethenoguanosine-3', 5'-cyclic monophosphate (8-Br-PET-cGMP), 8-Bromo-(2-naphthyl-1, N2-etheno)guanosine-3', 5'-cyclic monophosphate (8-Br-(2-N)ET-cGMP), 8-(4-Hydroxyphenylthio)-β-phenyl-1, N²-ethenoguanosine-3', 5'-cyclic monophosphate (8-pHPT-PET-cGMP), 8-(4-Chlorophenylthio)-β-phenyl-1, N²-ethenoguanosine-3', 5'-cyclic monophosphate (8-pCPT-PET-cGMP), 2-naphthyl-1, N2-ethenoguanosine-3', 5'-cyclic monophosphate ((2-N)ET-cGMP), β-Phenyl-1, N²-ethenoguanosine-3', 5'-cyclic monophosphate (PET-cGMP), 4-Methoxy-β-phenyl-1, N²-ethenoguanosine-3', 5'-monophosphate (pMeO-PET-cGMP), and pharmaceutically acceptable salts thereof wherein the cation can be any physiologically acceptable metal cation or a trialkylammonium ion, e.g. a sodium or calcium salt.

Ligands for Targeting to a Glutathione Transporter

A nanocontainer according to the invention comprises a ligand for a glutathione (GSH) transporter for targeting the nanocontainer to, into and/or across cells expressing the transporter. Thus, preferably the GSH transporter mediates at least one of specific binding, endocytosis and transcytosis of the ligand and the nanocontainer comprising the ligand into and/or through a target cell expressing the transporter. Transporter- or receptor-mediated delivery is one possible targeted drug delivery technique that was developed in recent years. It has the potential advantage of high specificity of delivery to target cells which express a receptor/transporter for the ligand that is conjugated with a drug or a drug carrier. The specific targeting of low molecular weight, as well as polypeptide and nucleic-acid based therapeutic or diagnostic agents, and nanocontainers comprising these agents, to cells and tissues may be enhanced greatly through the use of transporter/receptor-mediated delivery.

In one embodiment the ligand in the nanocontainers of the invention is a ligand for a GSH transporter that is expressed on endothelial cells of a blood-tissue barrier, including e.g. the blood-ocular barrier, a barrier created by endothelium of capillaries of the retina and iris, ciliary epithelium and retinal pigment epithelium (RPE). It consists of the following components: blood-aqueous barrier: the ciliary epithelium and capillaries of the iris, and the blood-retinal barrier (BRB): non-fenestrated capillaries of the retinal circulation and tight-junctions between retinal pigment epithelial cells preventing passage of large molecules from choriocapillaris into the retina, the blood-testes barrier, the blood-placenta barrier, and blood-CNS barriers, such as e.g. the blood-brain barrier, the blood-cerebral spinal fluid (CSF) barrier, the pial vessel-CSF barrier, the ependyma and glia limitans, the blood-nerve barrier, and the blood-spinal cord barrier. A preferred ligand is a ligand for a GSH transporter that is expressed on endothelial cells of the blood-retinal barrier. Use of such ligands will allow the specific delivery, or specifically enhanced delivery, of such targeted agents to the retina for the treatment of retinal diseases. Receptor-mediated targeting may further be combined with non-specific drug delivery systems (like protein conjugates, PEGylation, nanoparticles, liposomes, and the like) to greatly improve the pharmacokinetic and biodistribution properties of the drugs, which will significantly redirect the drugs specifically to receptor-expressing cells, tissues and organs, including the ones protected by specific blood-tissue barriers like e.g. the retina, the CNS, the blood-brain barrier (BBB), placenta and the testes.

In a preferred embodiment therefore, the ligand that is to be incorporated in the nanocontainers of the invention, is a ligand for an endogenous GSH transporter on a target cell. The ligand preferably is a ligand for a GSH transporter of a vertebrate target cell, more preferably a GSH transporter of a mammalian target cell, and most preferably a GSH transporter of a human target cell. The ligand preferably is a ligand that specifically binds to the GSH transporter. More preferably, the ligand specifically binds to the Na-dependent GSH transporter as present in human cerebrovascular endothelial cells as described by Kannan et al. (2000, Brain Res. 852(2):374-82). The term "specific binding", e.g. of a ligand to a transporter, as used herein, means binding that is measurably different from a non-specific interaction. Specific binding can be measured, for example, by determining binding of a molecule (ligand) compared to binding of a control molecule (control ligand), which generally is a molecule of similar structure that does not have binding activity, for example, a peptide of similar size that lacks a specific binding sequence. Specific binding is present if a ligand has measurably higher affinity for the receptor than what the control ligand has. Specificity of binding can be determined, for example, by competition with a control ligand that is known to bind to a target. The term "specific binding," as used herein, includes both low and high affinity specific binding. Specific binding can be exhibited, e.g., by a low affinity targeting agent having a Kd of at least about $10^{-4}$ M. E.g., if a receptor has more than one binding site for a ligand, a ligand having low affinity can be useful for targeting the microvascular endothelium. Specific binding also can be exhibited by a high affinity ligand, e.g. a ligand having a Kd of at least about of $10^{-7}$ M, at least about $10^{-8}$ M, at least about $10^{+9}$ M, at least about $10^{-10}$ M, or can have a Kd of at least about $10^{-11}$ M or $10^{-12}$ M or greater. Both low and high affinity-targeting ligands are useful for incorporation in the nanocontainers of the present invention.

Specific binding of a ligand to a transporter preferably is as defined herein above. In another embodiment the ligand is a ligand that is endocytosed and/or transcytosed into and/or through the target cell as may be assayed by a cell culture model of the BBB (using primary isolated bovine brain capillary endothelial cells (BCEC)) as described by Gaillard et al. (2001, Eur J Pharm Sci. 12(3): 215-222), or of the BRB (using primary isolated bovine retinal capillary endothelial cells (BREC)) as described by Wisniewska-Kruk et al. (2012, Exp Eye Res. 96(1): 181-90)), or similar models using e.g., human cerebral capillary endothelial cell line (hCMEC/D3), RBE4 cells, or MDCK cells as target cells. A ligand that is endocytosed and/or transcytosed into and/or through the target cell is herein defined as a ligand that is endocytosed or transcytosed into or through a BCEC or MDCK target cell at a rate that is at least 5, 10, 20 or 50% enhanced as compared to control conditions selected from a) cells lacking expression of GSH transporters; b) cells pre-treated with excess of free GSH; and c) a reference compound lacking a GSH moiety; when measured at 15, 30, or 60 minutes or 1, 2, 4, 8, or 18 hours or less after addition of the ligand to the target cell. Alternatively, endocytosis and/or transcytosis of GSH transporter-targeted ligands may be assayed by in vivo bioimaging techniques using for instance near-infrared dyes or radioactive labels conjugated thereto, resulting in at least 10, 20, or 50% enhanced retention in CNS area of the ligand at given time-points (based on region of interest (ROI) pixel quantification), as compared to appropriate control conditions (e.g., comparison to reference compounds lacking GSH moieties).

Preferred ligands that bind to the GSH transporter, for use in accordance with the present invention include e.g. ligands selected from the group consisting of: glutathione (GSH or gamma-glutamylcysteinylglycine), S-(p-bromobenzyl)glutathione, gamma-(L-gamma-azaglutamyl)-S-(p-bromobenzyl)-L-cysteinylglycin, S-Butylglutathione, S-Decylglutathione, Glutathione reduced ethyl ester, Glutathionesulfonic acid, S-Hexylglutathione, S-Lactoylglutathione, S-Methylglutathione, S-(4-Nitrobenzyl)glutathione, S-Octylglutathione, S-Propylglutathione, n-butanoyl gamma-glutamylcysteinylglycine (also known by the abbreviation GSH-C4) or the ethanoyl, hexanoyl, octanoyl or dodecanoyl derivatives thereof (also known by the abbreviations GSH-C2, GSH-C6, GSH-C8 and GSH-C12, respectively), GSH monoisopropyl ester (also known as N—(N-L-glutamyl-L-cysteinyl)glycine 1-isopropyl ester sulfate monohydrate or YM737), and GSH derivatives as described in U.S. Pat. No. 6,747,009 of the formula V:

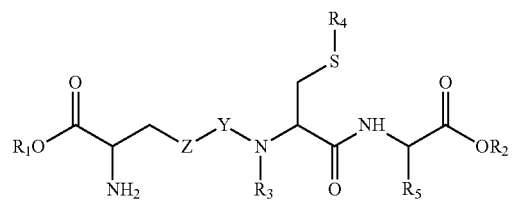

wherein Z=$CH_2$ and Y=$CH_2$, or Z=O and Y=CO;
$R_1$ and $R_2$ are independently selected from the group consisting of H, linear or branched alkyl (1-25C), aralkyl (6-26C), cycloalkyl (6-25C), heterocycles (6-20C), ethers or polyethers (3-25C), and where $R_1$-$R_2$ together have 2-20C atoms and form a macrocycle with the remainder of formula I;
$R_3$ is selected from the group consisting of H and $CH_3$;
$R_4$ is selected form the group consisting of 6-8C alkyl, benzyl, naphthyl and a therapeutically active compound; and,
$R_5$ is selected from the group consisting of H, phenyl, $CH_3$- and $CH_2$-phenyl; or,
a pharmaceutically acceptable salt thereof,
In a preferred embodiment $R_3$ in the formula above is H. In a further preferred embodiment $R_4$ in formula IV above is benzyl. In yet a further preferred embodiment $R_5$ in formula IV above is phenyl.

In one preferred embodiment of the invention, the ligand is conjugated or synthesized via the N-terminal amino acid residue, i.e. the amine group of the glutamic acid residue.

In another preferred embodiment of the invention, the ligand is conjugated or synthesized via the C-terminal amino acid residue, i.e. the carboxyl group of the glycine residue.

In yet another preferred embodiment of the invention, the ligand is conjugated or synthesized via the thiol (SH) group of the cysteine moiety.

Nanocontainers

The ligands in the nanocontainers of the invention are preferably conjugated to pharmaceutically acceptable nanocontainers that comprise a therapeutic or diagnostic agent. In such conjugates, the therapeutic or diagnostic agent may e.g. be encapsulated within nanocontainers, such as nanoparticles, liposomes or nanogels, whereby the ligand is preferably conjugated coupled to such a nanocontainer. Such conjugation to the nanocontainer may be either directly or via any of the well-known polymeric conjugation agents such as sphingomyelin, polyethylene glycol (PEG) or other organic polymers. For intravitreally injected nanocontainers, also nanocontainers without a ligand conjugated thereto can be used. Details of producing such pharmaceutical compositions comprising targeted (PEG) liposomes are e.g. described in U.S. Pat. No. 6,372,250. Thus, in a preferred embodiment a nanocontainer according to invention is at least one of a carrier protein, a liposome, a polyplex system, a lipoplex system, and, polyethyleneglycol.

A preferred nanocontainer for encapsulating the therapeutic or diagnostic agent, and conjugation to the ligand in accordance with the invention, is a liposome. Liposomes suitable for use in the nanocontainers of the invention include those composed primarily of vesicle-forming lipids. Vesicle-forming lipids, exemplified by the phospholipids, form spontaneously into bilayer vesicles in water at physiological pH and temperatures. The liposomes can also include other lipids, incorporated into the lipid bilayers, with the hydrophobic moiety in contact with the interior, hydrophobic region of the bilayer membrane, and the head group moiety oriented toward the exterior, polar surface of the bilayer membrane. The vesicle-forming lipids are preferably ones having two hydrocarbon chains, typically acyl chains, and a head group, either polar or nonpolar. There are a variety of diacyl synthetic vesicle-forming lipids and naturally-occurring vesicle-forming lipids, such as phospholipids, diglycerides, dialiphatic glycolipids, single lipids such as sphingomyelin and glycosphingolipid, cholesterol and derivatives thereof, alone or in combinations and/or with or without liposome membrane rigidifying agents. As defined herein, "phospholipids" include phosphatidylcholine (PC), phosphatidylethanolamine (PE), phosphatidic acid (PA), phosphatidylinositol (PI), phosphatidylserine (PS), sphingomyelin, plasmalogens, and phosphatidylcholine lipid derivatives where the two hydrocarbon chains are typically between about 14-22 carbon atoms in length, and have varying degrees of unsaturation.

The use of lipids with high transition temperatures and the incorporation of cholesterol (CHOL) and lipid conjugates such as distearoylphosphatidylethanolamine polyethylene glycol (DSPE-PEG), lead to a significant decrease of leakage of the encapsulated drugs during blood circulation or in the extracellular milieu. Moreover, such lipids also reduce non-specific interactions between the liposomes and serum proteins (opsonins), thus preventing liposome clearance by the cells of the reticuloendothelial system (RES), increasing circulation time for optimizing the interaction of the system with the target cells (Allen, 1987; Gabizon, 1992). Examples of phospholipids having a phase transition temperature of 37° C. or higher include e.g. hydrogenated purified egg phosphatidylcholine (HEPC; phase transition temperature: 50-60° C.), hydrogenated purified soybean phosphatidylcholine (HSPC; phase transition temperature: approximately 55° C.), dipalmitoyl phosphatidylcholine (DPPC; phase transition temperature: approximately 41° C.), and distearoyl phosphatidylcholine (DSPC; phase transition temperature: approximately 58° C.). Of these, HSPC is more preferred. These phospholipids can be used singly or in combination of two or more types. The liposome used in the present invention can further comprise a stabilizing agent such as cholesterol or a cholesterol derivative. The molar ratio between a cholesterol derivative and a phospholipid is preferably 1:0.3 to 3, more preferably 1:1 to 2.5, and most preferably 1:1.2 to 1.8 or around 1:1.5.

The average size of the liposome is preferably between, 50 and 200 nm, more preferably between 80 and 150 nm and most preferably between 100 and 120 nm, with a polydispersity (PdI) of less than 0.2, 0.15 or 0.1.

Liposomes can be loaded with the active ingredient by two methods, passive and active (remote) loading. The liposome lipid bilayer is a semi-permeable barrier that blocks the diffusion of charged and larger non-charged molecules, while small non-charged substances can penetrate freely. In passive loading, a membrane impermeable drug is dissolved in the hydration solution during the liposome manufacturing process. Upon addition of the aqueous solution to a lipid mixture lipid bilayers form and partially encapsulate the drug solution to form liposomes. Most of the drug solution remains in the external solution and must be removed by dialysis or chromatography. Passive encapsulation is limited by the liposomal-trapped volume and drug solubility. Therefore, encapsulation efficiency (EE) is lower and usually does not exceed 5%. However, in principle any active ingredient can be encapsulated by passive loading. Active (remote) loading is therefore preferred. In active loading, as e.g. described in EP0825852, the drug is be encapsulated by active methods after formation of the liposomes, which can result in trapping efficiencies approaching 100%. However, only drugs that are amphipathic weak acid or basic qualify for remote loading. Encapsulation of these molecules is based on the fact that ionized molecules are less membrane permeable compared to their unionized species. Therefore, provoking intraliposomal ionization of the drug by a pH gradient causes trapping of the compound, leading to a high intra- to extraliposomal drug concentration ratio. As shown in the Examples herein Rp-8-Br-PET-cGMPS can be efficiently encapsulated into liposomes by active loading.

The ligand can be conjugated to the nanocontainers of the invention directly or via any of a conjugation agent, preferably a polymeric conjugation agent. Polyethylene glycol (PEG) is a preferred conjugation agent. The PEG preferably has a polymerization number (n) of about 6-210. The molecular weight of the conjugation agent is preferably between 300 and 50,000 Da, more preferably between 750 and 10,000 Da, and most preferably between 1,000 and 5,000 Da, e.g. around 2000 Da.

A preferred conjugation agent is a bifunctional conjugation agent, which contains a lipid at one end and the ligand for a GSH transporter at the other end. The lipid end of the PEG attaches conjugation agent to the liposome by interacting with and/or inserting into the lipid bilayer. The lipid end of the conjugation agent can comprise a vitamin E derivative or a phospholipid. Preferred vitamin E derivative are e.g. described in EP05292820. The phospholipid at the lipid end of the conjugation agent may have the following formulae:

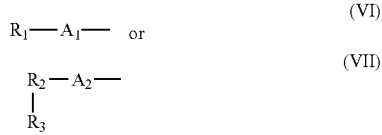

In formula (VI), $A_1$ is sphingosine and $R_1$ may comprise octanoyl or palmitoyl. In formula (VII), $A_2$ is phosphoethanoamine and $R_2$ and $R_3$ may comprise myristoyl, palmitoyl, stearoyl, or oleoyl, whereby $R_2$ and $R_3$ can be the same or different. When PEG is bonded to the phospholipid derivatives represented by formula (VI), it preferably has a molecular weight of about 750-5,000 Da, and when PEG is bonded to the phospholipid derivatives represented by formula (VII), it preferably has a molecular weight of about 350-5,000 Da.

At the end opposite the lipid end, the PEG preferably is derivatised to comprise carboxylic acid, a maleimide, or an amide for covalently linking the ligand for a GSH transporter. A preferred conjugation agent is obtainable by reacting 1,2-distearoyl-sn-glycero-3-Phosphoethanolamine-polyethylene glycol-maleimide (DSPE-PEG-MAL) with a ligand for a GSH receptor having a maleimide-reactive thiol group. DSPE-PEG-maleimide is commercially available in molecular weights of e.g. 1,000, 2,000, 3,400, 5,000 10,000 and 20,000, of which DSPE-PEG(2000)-maleimide is preferred.

Preferably from 5 to 1000 conjugation agents are conjugated to each liposome. More preferably, approximately at least 10, 20, 30 or 40 conjugation agents and no more than 200, 100 or 50 conjugation agents are conjugated to each liposome.

Use of the Nanocontainers

In a further aspect, the nanocontainers of the invention are used as a medicament.

The nanocontainers of the invention are preferably used for the treatment and/or prevention of a pathology, condition or disorder associated with dysregulation of a cGMP-effected cellular target, wherein preferably the target is at least one of a cGMP-dependent protein kinase (PKG) and a cGMP-gated channel (CNGC). Schlossmann and Schinner (2012, Arch Pharmacol, 385:243-252) and Wolfertstetter et al. (2013, Pharmaceuticals 2013, 6: 269-286) review whether inhibition or activation of at least one of or both of the PKG and CNGC is the appropriate biological task in the treatment of a particular pathology, condition or disorder. In accordance therewith a cGMP analogue may be chosen capable of performing this biological task as set out above for the different analogues. It is to be understood herein that the treatment of a pathology, condition or disorder also includes the prevention thereof, even if not explicitly mentioned, unless specifically otherwise indicated.

Preferably the nanocontainers of the invention are used for treating or preventing a disease or condition of the retina. Diseases and conditions of the retina are preferably treated with the nanocontainers of the invention comprising cGMP analogue that inhibit at least one of PKG and CNGC, such as e.g. Rp-8-Br-PET-cGMPS and Rp-8-pCPT-PET-cGMPS, and include rare hereditary diseases of the retina such as retinitis pigmentosa, Stargardt's disease, fundus flavimaculatus, juvenile Best's disease, adult vitelliform foveomacular dystrophy (adult vitelliform degeneration), familial drusen (North Carolina macular dystrophy), Bietti's crystalline dystrophy, progressive cone dystrophies, Alport's syndrome, benign familial fleck retina, Leber's congenital amaurosis, congenital monochromatism and hereditary macular dystrophies.

In addition, these nanocontainers of the invention, preferably comprising cGMP analogue that inhibit at least one of PKG and CNGC, such as e.g. Rp-8-Br-PET-cGMPS and Rp-8-pCPT-PET-cGMPS, may be used to treat secondary pigmentary retinal degeneration as it occurs in a number of metabolic and neurodegenerative diseases, various syndromes and other eye diseases, including: retinitis pigmentosa and hearing loss also are associated with Usher syndrome, Waardenburg's syndrome, Alstrom's syndrome, Alport's syndrome, Refsum's syndrome, and other systemic conditions, all of which have their own systemic manifestations, short stature, renal dysfunction, and polydactyly are some signs of Bardet-Biedl syndrome or Laurence-Moon syndrome when associated with pigmentary retinopathy, the mucopolysaccharidoses may be associated with retinitis pigmentosa (e.g., Hurler's syndrome, Scheie's syndrome, Sanfilippo's syndrome), as well as the mitochondrial disorder Kearns-Sayre syndrome. In addition to those mentioned above, these include: Friedreich's ataxia, mucopolysaccharidosis, muscular dystrophy (myotonic dystrophy), Batten's syndrome, Bassen-Kornzweig syndrome, homocystinuria, oxalosis, eye and retinal trauma, glaucoma with retinal pigment epithelial changes, end-stage chloroquine retinopathy, end-stage thioridazine retinopathy, end-stage syphilitic neuroretinitis and cancer-related retinopathy. These nanocontainers of the invention may also be used to treat other common diseases of the retina such as e.g. diabetic retinopathy, age related macular degeneration, macular Hole/Pucker, ocular malignancies, such as retinoblastoma, retinal detachment and river blindness/Onchocerciasis.

Furthermore the nanocontainers of the invention may be used to treat entirely different conditions that are associated with dysregulation of at least one of a cGMP-dependent protein kinase (PKG) and a cGMP-gated channel (CNGC) such as neuronal or neurodegenerative disorders, anosmia, inflammatory and neuropathic pain, axonal regrowth and recovery after spinal cord injury (Henkin et al., 2008, Clin Invest Med. 31:E78-84; Schmidtko et al., 2008, J Neurosci. 28:8568-76; Ter-Avetisyan et al., 2014, J Neurosci. 34:737-47; Senturk et al., 2014: Br J Neurosurg. 7:1-6). Also cardiovascular diseases, hypertension (PKG activators), hypotension (PKG inhibitors), angina pectoris, pulmonary hypertension, erectile dysfunction, ischemic stroke, atherosclerosis, acute shock, and cancer (see e.g. Wang et al., 2012, J. Cell. Biochem. 113: 3587-3598; Karakhanova et al., 2014, Pancreas, 43:784-794; Francis et al., 2010, Pharmacol Rev. 62:525-63). This also includes certain parasitic diseases like malaria, sleeping disease (African trypanosomiasis), and Chagas disease, in which the parasite survival is critically depending on PKG activity (Taylor et al., 2010, Eukaryot Cell. 9:37-45).

In another aspect, the invention relates to a method for treating or preventing any of the above pathologies, conditions or disorders by administration of a therapeutically or prophylactically effective amount of (a pharmaceutical composition comprising) a nanocontainer of the invention, to a subject in need of prophylaxis or therapy.

The GSH targeting of the nanocontainers of the invention to and across the blood-ocular barrier allows systemic administration of the nanocontainers and efficient delivery of the therapeutic and/or diagnostic agents to the retina. The nanocontainers of the invention are thus preferably administered systemically or through the blood stream. Alternatively, or in addition, the nanocontainers of the invention may be administered locally.

Preferably the nanocontainers of the invention are administered parenterally. The parenteral route for administration of the nanocontainers is in accord with known methods, e.g. injection or infusion by preferably intravenous, intraperitoneal or intraarterial routes. Alternatively, to prevent unnecessary systemic exposure, suprachoroidal or retrobulbal injections delivering the nanocontainer, e.g. liposomes, for instance directly to the choriocapillaris behind the eye may be used. Another alternative route of parenteral administration are direct intravitreal injections. In this case, either GSH-conjugated nanocontainers can be used, but also nanocontainers without a targeting ligand may be employed, such as PEGylated liposomes, since in such case the nanocontainer can act as a reservoir and slowly release the encapsulated drug at the site of action, thereby reducing the need for repeated administration, or allowing to reduce the frequency of repeated administration.

Alternatively, or in addition, the nanocontainer is administered by topical or ocular application. Preferably, the nanocontainer is administered by using conventional eye drops.

In a further aspect, the invention relates to a pharmaceutical composition. The pharmaceutical composition of the invention comprises a nanocontainer as defined herein above. The composition further preferably comprises a pharmaceutically acceptable carrier, medium or delivery vehicle as are conventionally known in the art. Pharmaceutically acceptable solvents, stabilizing agents, osmotic agents, buffering agents, dispersing agents, and the like may also be incorporated into the pharmaceutical compositions. The preferred form depends on the intended mode of administration and therapeutic application. The pharmaceutical carrier can be any compatible, non-toxic substance suitable to deliver the active ingredients, i.e. the nanocontainer of the invention to a patient or subject.

Preparation with the nanocontainers for parenteral administration must be sterile. Sterilisation is readily accomplished by filtration through sterile filtration membranes, prior to or following lyophilisation and reconstitution. The nanocontainer is administered continuously by infusion or by bolus injection. A typical composition for intravenous infusion could be made up to contain 10 to 500 ml of sterile 0.9% NaCl or 5% glucose optionally supplemented with a 20% albumin solution and the required dose of the nanocontainer. Alternatively, the nanocontainer can be dissolved in Phosphate buffer saline (PBS). A typical pharmaceutical composition for intravenous, intraperitoneal or intraarterial injection would be made up to contain, for example, 1-10 ml of sterile physiological buffered aqueous solution and the required dose of the nanocontainer of the invention. Methods for preparing parenterally administrable compositions are well known in the art and described in more detail in various sources, including, for example, Remington's Pharmaceutical Science (Ed. AR Gennaro, 20th edition, 2000, Williams & Wilkins, PA, USA; incorporated by reference in its entirety for all purposes).

The nanocontainers of the invention are preferably administered in doses of between 0.1 and 1000 mg/kg once per 1 or 2 days. Preferably the dosage range has a lower limit of at least 0.1, 0.2 0.5, 1, 2, 10, 20, 50 or 100 mg/kg once per 1 or 2 days and an upper limit of no more than 1000, 500, 200 or 100 mg/kg once per 1 or 2 days. The doses indicated correspond to the amount of the therapeutic agent (e.g. the cGMP analogues) as comprised in the nanocontainer and not to the entire nanocontainer composition. Alternatively, the nanocontainers of the invention are administered intravitreally once per two weeks or once per 6 weeks. Preferably the dosage range for intravitreal injection has a lower limit of at least 25 µl (2 mg/ml) once per 6 weeks and an upper limit of no more than 200 µl (4 mg/ml) once per two weeks.

For therapeutic applications, the pharmaceutical compositions comprising the nanocontainers of the invention are administered to a patient suffering from a pathology, condition or disorder as described above in an amount sufficient to reduce the severity of symptoms and/or prevent or arrest further development of symptoms. An amount adequate to accomplish this is defined as a "therapeutically-" or "prophylactically-effective dose". Such effective dosages will depend on the severity of the condition and on the general state of the patient's health.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the elements is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

BRIEF DESCRIPTION OF THE FIGURES

FIGS. 1A and 1B. In vitro protective effects of DF003 (Rp-8-Br-PET-cGMPS) and LP-DF003 (Rp-8-Br-PET-cGMPS encapsulated in GSH-conjugated liposomes prepared as described in Example 1). DF003 significantly reduced the death of rd1 photoreceptor-like cells, at concentrations as low as 100 nM. This effect was increased by LP-DF003, which was still effective when it was used to yield a dose that corresponded to 10 nM of DF003. At the same time wild-type (wt) photoreceptor-like cells were not affected by either DF003 or LP-DF003, even at the highest concentration used (50 µM). B) Similarly, DF003 reduced photoreceptor death in organotypic rd1 retinal explant cultures, while it showed no signs of toxicity in wt explant cultures.

EXAMPLES

Figure 1A:
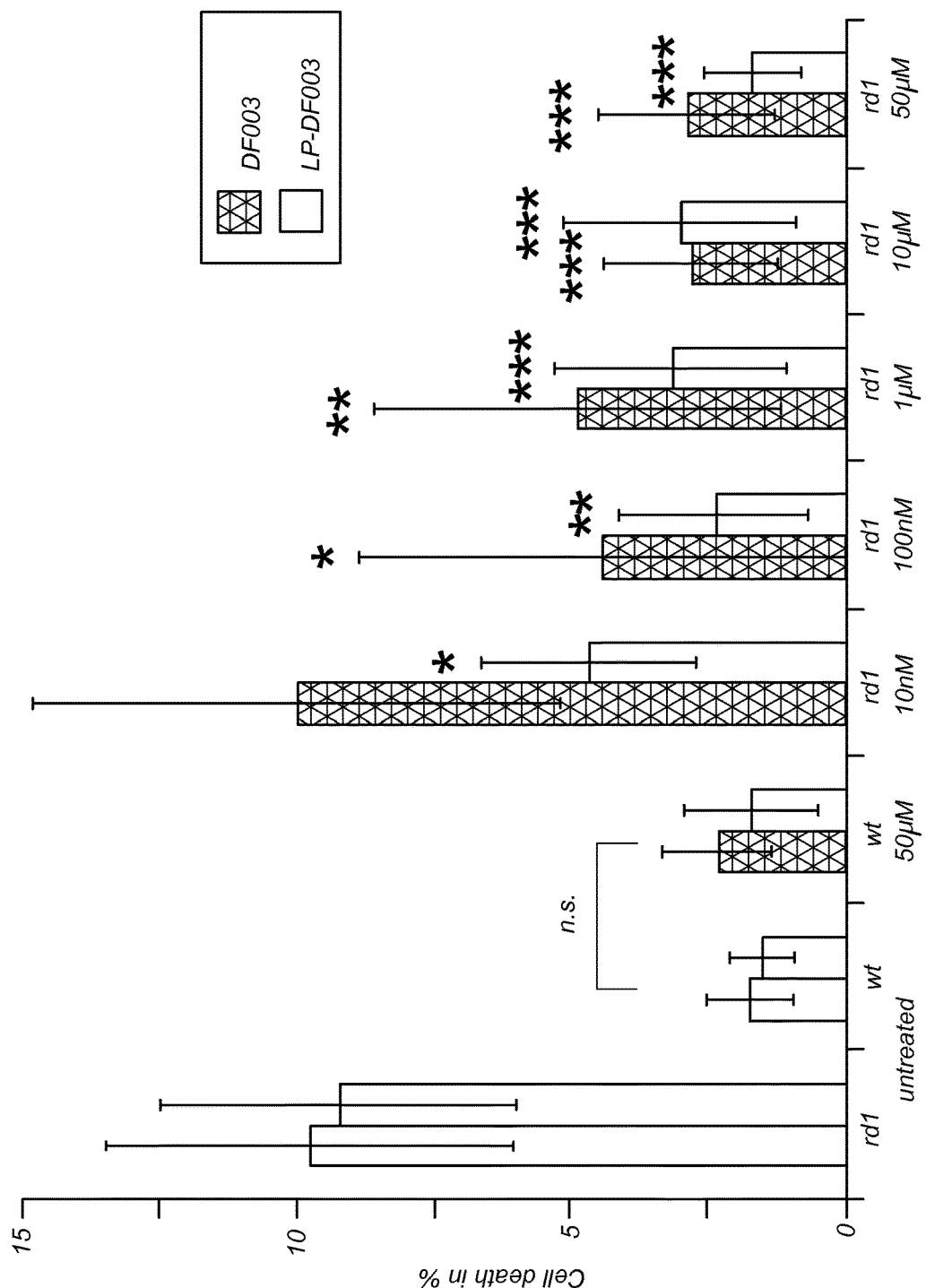

1. Materials and Methods
1.1 Production of GSH-Conjugated Liposomes Encapsulating cGMPS First, micelles were prepared by mixing (molar ratio 1:1.5) DSPE-PEG2000-maleimide (NOF, Grobbendonk, Belgium, 916 mg in 36.72 mL of DI water) with glutathione (Sigma-Aldrich, Zwijndrecht, the Netherlands, 144 mg in 4.42 mL of DI water) at room temperature for 2 h. Next, micelles were added to calcium acetate hydrate (4094 mg in 57.36 mL of DI water; final concentration 200 mM) and kept at 60° C. for 30 minutes.

2808 mg of HSPC (Hydrogenated Soy Phosphatidylcholine; final concentration 28 mM) and 912 mg of cholesterol (final concentration 18.6 mM) were dissolved in 30.96 mL ethanol in a serum bottle, mixed with the micelles while stirring and incubated in a water bath for 30 min at 60° C. Finally, the liposomes were extruded using 0.2/0.2 μm PC membrane (2 times), 0.2/0.1 μm PC membrane (2 times) and 0.1/0.1 μm PC membrane (2 times) at 60° C. and stored at 4° C. The size of liposomes was measured with 10 μL of the liposomal suspension diluted in 1 ml PBS by the dynamic light scattering method (Zetasizer Nano ZS, Malvern, Worcestershire, UK). The average size of the liposome batches was between 100 and 120 nm, PdI<0.1. After size was measured the calcium acetate liposomes were purified from non-encapsulated calcium acetate hydrate using dialysis system TFF (Millipore Cogent μScale and Millipore Pellicon cassette 50 cm$^2$). The liposomes were dialyzed against 7 volumes of saline (0.9% NaCl). The batch was concentrated back to start volume 120 mL using dialysis with a TFF system and analyzed for lipid content and size.

LP-DF003 was generated by remote loading of the calcium acetate GSH-PEG-liposomes with DF003 (Rp-8-Br-PET-cGMPS) at a drug/phospholipid molar ratio 0.3. For this 1 volume of DF003 dissolved in MilliQ (40 mg/mL) was mixed with 9 volumes of liposomes (HSPC 20 mg/mL, both pre-warmed at 60° C.) and incubated at 60° C. for 45 min. Subsequently, the batch was stored at 4° C., purified and analyzed. Purification was done by dialysis using a TFF system. The LP-DF003 liposomes were dialyzed against 10 volumes of saline, concentrated to a DF003 concentration of 3 mg/mL and sterile filtered with 0.2 μm filter (Corning sterile syringe filter) and stored at 4° C. Encapsulated DF003, i.e. LP-DF003, and other liposome constituents were analyzed by HPLC.

For encapsulation Sp-8-Br-PET-cGMPS and 8-Br-PET-cGMP by remote loading essentially the same procedure is applied as above for encapsulation of LP-DF003.

Encapsulation by remote loading of DF001 (Rp-8-Br-cGMPS), DF002 (Rp-8-pCPT-cGMPS) and Rp-8-pCPT-PET-cGMPS was also tested, using several experimental conditions (including drug-lipid ratio, extraliposomal pH, intraliposomal pH, and intraliposomal calcium acetate concentration) were screened to facilitate and sustain the encapsulation of these drugs. In contrast to DF003, encapsulation by remote loading of DF001, DF002 and Rp-8-pCPT-PET-cGMPS was not possible.

Rp-8-Br-cGMPS, Rp-8-pCPT-cGMPS, Rp-8-Br-PET-cGMPS (DF003) and Rp-8-pCPT-PET-cGMPS were obtained from BIOLOG Life Science Institute GmbH, Bremen, Germany.

1.2 Animals for In Vitro Retinal Explant Culture and for In Vivo Studies

Animals for preparation of primary retinal cell cultures were kept at CSSI (Centro Servizi Stabulario Interdipartimentale) of University of Modena and Reggio Emilia. The protocol was approved by the Ethical Committee of University of Modena and Reggio Emilia (Prot. N. 106 22 Nov. 2012) and by Italian Ministero della Salute. Animals for in vitro retinal explant studies were kept at the Lund University department for clinical sciences. Here, we used the rd1 and rd2 retinitis pigmentosa model mice with corresponding wild-type (wt) controls. Animals were kept under standard white cyclic lighting, with ad libitum access to food and water, and were used irrespective of gender. All procedures were performed in accordance with the Swedish animal care and ethics committees. Efforts were made to keep the number of animals used and their suffering to a minimum.

Animals for in vivo studies were kept in the Tubingen Institute for Ophthalmic Research internal animal housing facility, under standard white cyclic lighting, had free access to food and water, and were used irrespective of gender. C3H rd1/rd1 (rd1) and control C3H wild-type (wt) mice were for initial in vivo testing. After successful testing in rd1 animals, the in vivo testing was extended to further RD animal models for cross-model validation. These additional animal models were: C3H rd2/rd2 (rd2 or rds), C57Bl6J rd10/rd10 (rd10), C57Bl6J cpfl1/cpfl1 (cpfl1) mice, as well as Rho P23H rats. All in vivo procedures were performed in accordance with the local ethics committee at Tubingen University (§ 4 registrations from 29-04-10; 30-06-10; 11-03-11; animal permit AK5/12), and the ARVO statement for the use of animals in ophthalmic and visual research.

1.3 Primary Retinal Cell Culture Preparation, Differentiation and Treatment

Different doses of DF003 and LP-DF003 were tested in vitro on a primary culture of retinal cells derived from the rd1 mouse model. About 20-30% of the primary cells can be differentiated into rod photoreceptors (Demontis et al. 2012, PLoS One. 7, e33338; Giordano et al. 2007, Mol. Vis. 13, 1842-1850). Retinal stem cells from adult wt and rd1 mice were isolated from the ciliary epithelium after treatment with 2 mg/ml dispase (20 min) followed by 1.33 mg/ml trypsin 0.67 mg/ml, hyaluronidase and 0.13 mg/ml kynurenic acid (10 min) and cultured for a week in serum free medium containing 20 ng/ml basic FGF, 2 µg/ml heparin, 0.6% glucose, N2 hormone mix in DMEM-F12 to form neurospheres (Giordano et al., 2007, supra). Retinal neurospheres were then plated on glass slides coated with extracellular matrix (ECM, Sigma) in DMEM-F12 supplemented with 20 ng/ml FGF for 4 days. Cells were allowed to differentiate in DMEM-F12 supplemented with 1% FBS. rd1 differentiated retinal cells activated a cell death program at the 11$^{th}$ day of differentiation as previously published (Sanges et al. 2006, Proc. Natl. Acad. Sci. U.S.A 103, 17366-17371). Cells were exposed to different doses of LP-DF003 at day 10 of differentiation (one day before activation of cell death pathways). 16 hours after treatment with LP-DF003 cells were fixed with 4% paraformaldehyde for 10 min at room temperature. Cell death was evaluated by staining of cells for 2 minutes with 2 µM Ethidium homodimer and counterstaining of nuclei with DAPI (4',6-diamidino-2-phenylindole, Sigma). Slides were mounted with mowioll 4-88 (Sigma) and analysed at a Zeiss Axioskop 40 fluorescence microscope. Ethidium homodimer positive cells were counted in each slide and expressed as percentages of the total number of cells (DAPI stained) per slide. Paired Student's t-test analysis compared data derived from at least three different untreated and at least three different treated rd1 retina cells.

1.4 Organotypic Retinal Explant Culture

For biochemical analyses and comparisons between models and wt tissues, we typically use material from ages corresponding to the onset of retinal degeneration. Retinal tissue is obtained from post-natal day 5 (PN5) animals, from which, after sacrifice, the eyes are enucleated and retinae cultured as retinal explants. In brief, the retina with the retinal pigment epithelium (RPE) still attached is isolated and subsequently transferred to Millicell culture dish filter inserts (Millipore AB, Solna, Sweden; PIHA03050), with the RPE layer facing the culturing membrane. The explants are then incubated in custom made R16 nutrient medium at 37° C. The nutrient medium has a volume of 1.5 ml per dish, which is replaced with fresh medium usually every second day (unless the exact culturing paradigm requires otherwise) during the culturing period.

PN5 explants were allowed to adjust to culture conditions for two days in vitro (DIV), after which they were subjected to treatments of interest. At this point the treatment paradigm consisted of addition of medium with test compound every second day for four days reaching the equivalent to PN11 (labelled as short term treatment: PN5+2 DIV+4 DIV) or to PN19 (long term treatment: PN5+2 DIV+12 DIV).

At the end of the explant culturing period, the specimens were fixed in 4% paraformaldehyde in a phosphate-buffered salt solution for about 2 h in 4° C. The thus fixed eyes were cryoprotected in Sorensen's sucrose buffer, histological sectioning was performed using a cryotome, and 12 µm cryosections collected on microscope slides.

1.5 Drug Testing on In Vivo RD Animal Models

Before treatment with drug or drug/DDS combinations, the animals were anesthetized with diethyl-ether. For systemic treatment, 0.9% NaCl solution containing liposomal DDS/drug formulation were injected either into the tail vein (caudal vein; intravenous; i.v.; 50 µl) or into the peritoneum (intraperitoneal; i.p.; 200 µl) of the anesthetized animal. In rd10 mice, a local intravitreal (IVT) treatment was also tested. Here, the animals received a 0.5 µl injection into the vitreous body of one eye, while the other eye was kept as untreated, contralateral control. For both i.p. and IVT treatments a liposomal formulation not containing DF003 (i.e. "empty" liposomes) was used as an additional control.

The in vivo treatment was performed initially on rd1 animals, but later extended to other animal models (rd2, rd10, cpfl1, Rho P23H). Because of the different onset and progression of retinal degeneration in the different RD models, the treatment paradigms had to be adapted to each model. For details on these treatment paradigms see Table 1.

At various post-treatment time-points (see Table 1), in vivo optic coherence tomography (OCT) and scanning laser ophthalmoscopy (SLO) analysis was used for direct, non-invasive imaging of retinal morphology (OCT) and of fluorescently labelled drugs (SLO) or drug/DDS combinations to determine the distribution and uptake of drug in the retina. In addition, retinal function was assessed using electroretinographic (ERG) recordings. After non-invasive in vivo examinations, and between 1 to 12 days after treatment, experimental animals were killed by carbon dioxide asphyxiation. The eyes were immediately enucleated, fixed for 2 h in 4% PFA and prepared for cryosectioning or whole-mount preparation.

TABLE 1

In vivo treatment paradigms for five different RD models

| Animal model, Species | Treatment start | Treatment intervals/dosis | In vivo analysis | Treatment end |
|---|---|---|---|---|
| rd1 mouse | PN10 (i.v. + i.p. on the first day) | Once per day/ 200 µl | PN14, 18, (30) | PN17 |
| rd2 mouse | PN14 | Every 2$^{nd}$ day/ 200 µl | PN18, 30, 60 | PN59 |
| rd10 mouse | PN14 | Once per day/ 200 µl | PN18, 24, 30 | PN29 |
| rd10 mouse IVT | PN14 | PN14, 16, 18, 22, 26/0.5 µl | PN30 | PN26 |
| cpfl1 mouse | PN14 | Once per day/ 200 µl | PN24, 30 | PN29 |
| Rho P23H rat | PN14 | Every 4$^{th}$ day/ 400-3200 µl | PN30, 60, 120 | PN118 |

1.6 Quantification of Photoreceptor Cell Death and Survival

The read-outs for the in vitro and in vivo treatment experiments consisted of quantification of photoreceptor cells stained positive for the cell death marker TUNEL and/or counting of surviving photoreceptor rows, as seen in standard histological tissue stains. In both cases the results were captured by means of a microscope and digital camera, analysed manually or semi-automatically, and this was then followed by calculations for statistical significance of the recorded data in principle as published previously (Arango-Gonzalez et al. 2014, PLoS One. 9, e112142).

2. Results 2.1 In Vitro and In Vivo Protection of Photoreceptors by LP-DF003

Over 200 novel cGMP analogues generated, of which 140 were tested for their capacity to bind PKG in cell free assays (Zegzouti et al. 2009, Assay. Drug Dev. Technol. 7, 560-572). Of these, 33 compounds exhibiting strong PKG binding, were selected for further in vitro analysis in the 661W cell line and in photoreceptor-like cell cultures derived from retinitis pigmentosa mutant mice (Sanges et al. 2006, supra). This cell-based screening assay identified 11 compounds that could reduce cell death caused by retinitis pigmentosa mutations and thus showed photoreceptor protective activity. These 11 compounds were then further tested in organotypic retinal explant cultures (Sahaboglu et al. 2013, Cell Death & Disease 4) derived from either wild-type, rd1 (Sanyal and Bal 1973, Z. Anat. Entwicklungsgesch. 142, 219-238) or rd2 mice (Sanyal and Jansen 1981, Neurosci. Lett. 21, 23-26). Retinal tissue cultures narrowed down the number of cGMP analogues with promising neuroprotective effects to 4 compounds, which were found to significantly reduce cell death of rd1 and rd2 photoreceptors in vitro.

These 4 compounds were then tested in vivo in rd1 mice, and one of these in combination with the liposomal (LP) delivery system. LP-DF003 showed the most pronounced protective effects in rd1 animals and was then subjected to tests in two other in vivo mouse models for retinitis pigmentosa (rd2 and rd10 mice). Another long-term study (4 months) was performed in a fourth retinitis pigmentosa model, the P23H rat (data not shown).

In the different test systems DF003 yielded the following results: DF003 preserved the viability of diseased rd1 photoreceptors in cell and organotypic retinal tissue cultures (FIG. 1 A, B). In both systems, wild-type (wt) photoreceptors were not affected by DF003 treatment indicating that it was not toxic to these cells up to the concentration of 50 µM. LP-DF003 showed improved protective effects when compared to DF003 at lowed concentrations in photoreceptor-like cell cultures derived from retinitis pigmentosa mutant mice (FIG. 1A)

In organotypic retinal explants, no evidence of DF003 toxicity was found in the inner retina (data not shown). DF003 also prevented photoreceptor death in retinal explants of two other models, the more slowly degenerating rd10 model, which also has a Pde6b mutation, but at a different site than the rd1 model, as well as the even slower degenerating rd2 mouse model in spite of the very different mutation the rd2 mouse carries (data not shown, but see FIG. 2 FIGS. 2A and 2B for the in vivo data of rd10 and rd2). See also below for more details on these models. Similar observations were made for Sp-8-Br-PET-cGMPS.

Figure 4:
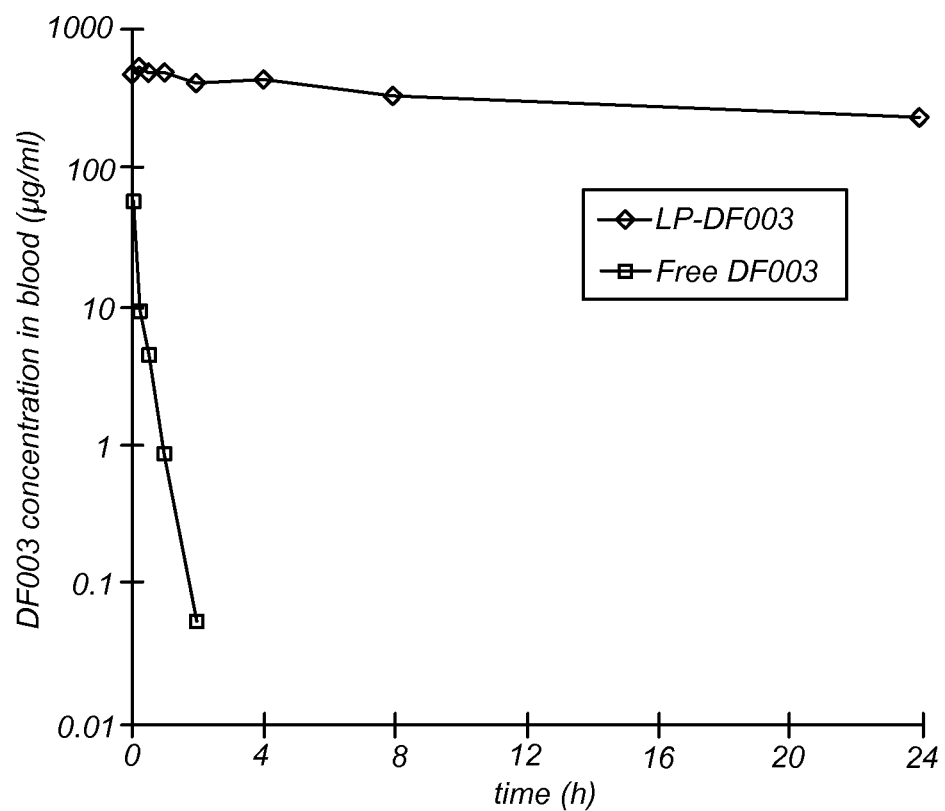
FIG. 4. Pharmacokinetics of DF003 and LP-DF003. A pharmacokinetic study in adult rats revealed a strong extension of the in vivo half-life of LP-DF003 vs. free DF003. While free DF003 had an in vivo half-life of around 15 min, LP-DF003 displayed a half-life time of approximately 24 hrs.
Figure 5A:
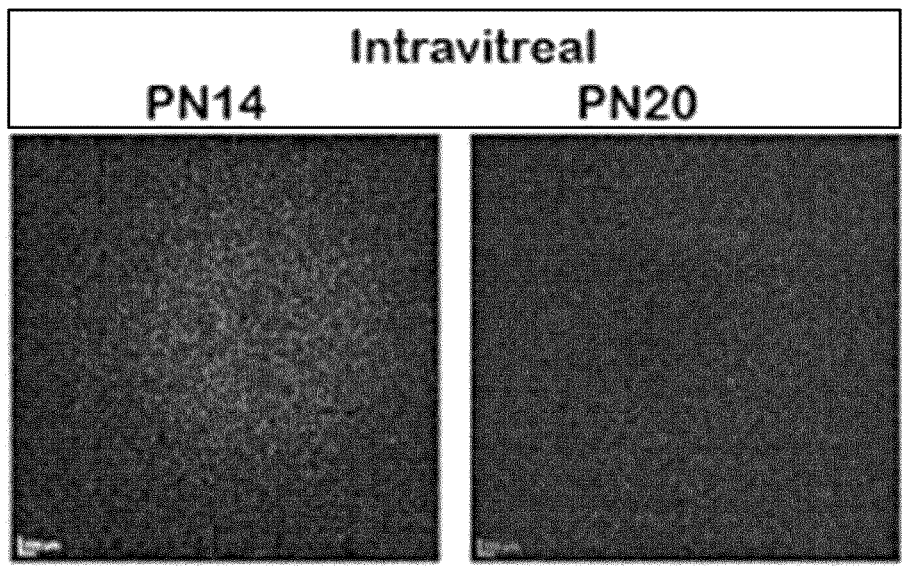
FIGS. 5A-5D. SLO imaging in vivo demonstrates successful delivery to the retina. Mice injected at postnatal day (PN) 10 with fluorescently labelled liposomal drug delivery system were analysed in vivo at PN14 and PN20 using scanning laser ophthalmoscopy (SLO). Topical application (not shown), and intravitreal (a) and subtenon (b) injection did not show significant retinal uptake of label. However, intravenous (c) and intraperitoneal (d) injection, both, resulted in a strong fluorescent labelling of retinal blood vessels and neuroretina at PN14, i.e. 4 days after application. At PN20 most of the label had disappeared, although after intraperitoneal injection defined retinal patches still showed some fluorescence.
Figure 5B:
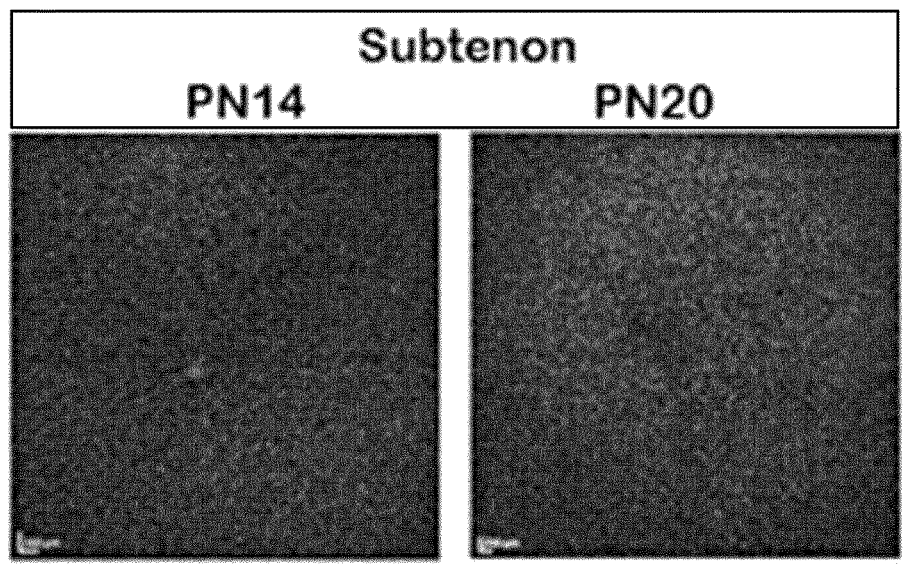
Figure 5C:
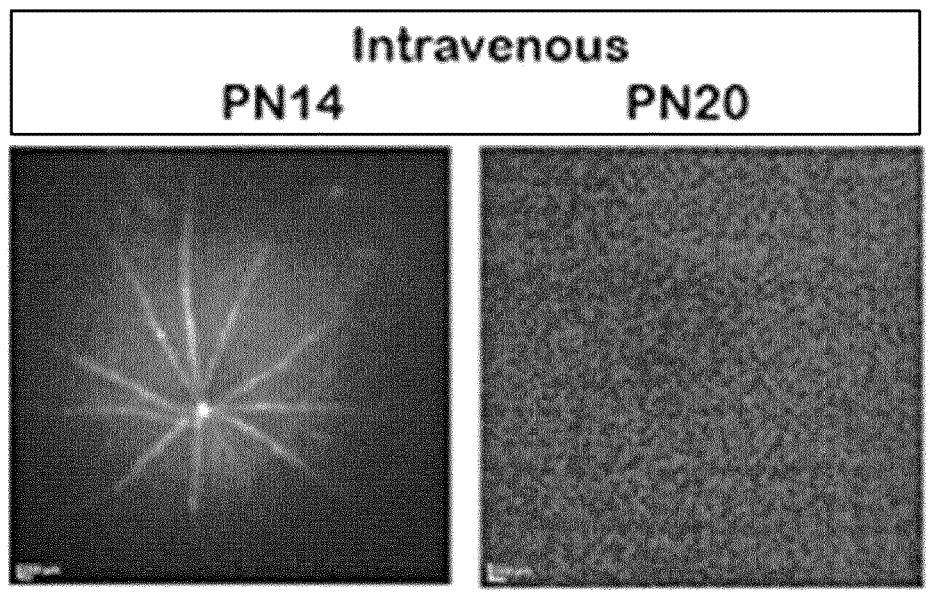
Figure 5D:
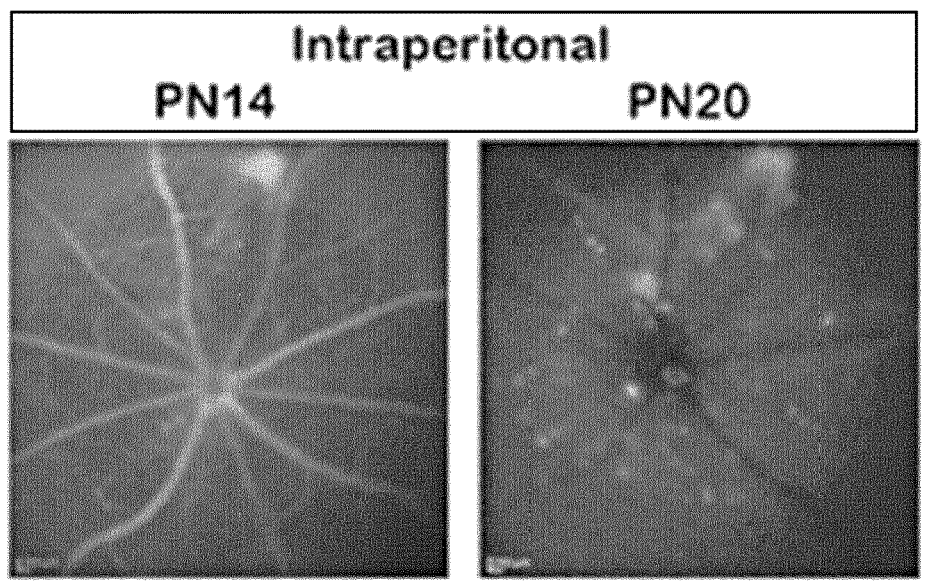

The bioavailability of DF003 in vivo was dramatically improved when it was used in its liposomal formulation LP-DF003 (cf. section 2.3; FIG. 4). Also the bioavailability of Sp-8-Br-PET-cGMPS improves when encapsulated into liposomes.

Figure 2A:
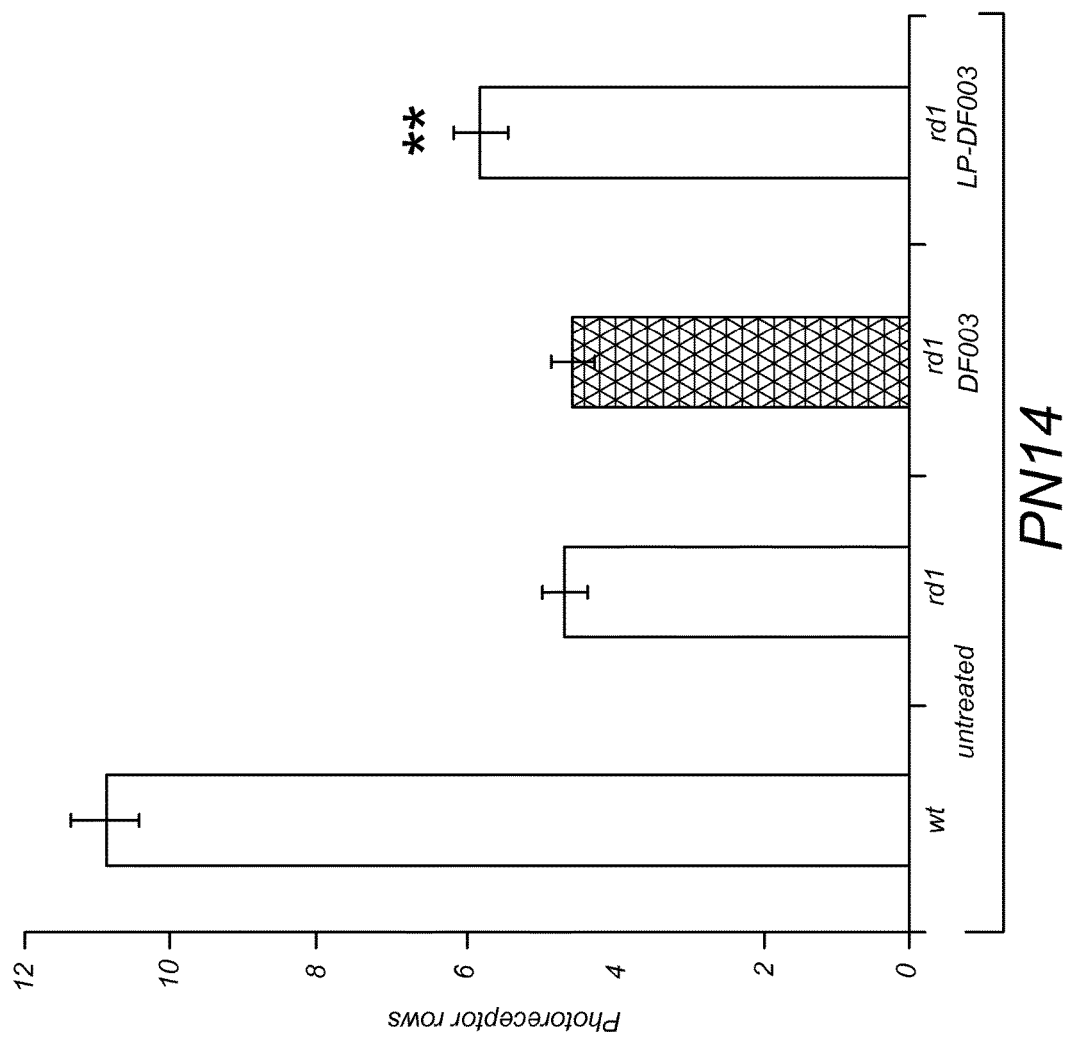
FIGS. 2A and 2B. LP-DF003 protects photoreceptors in three different retinitis pigmentosa animal models. Photoreceptor survival was assessed in three different in vivo retinitis pigmentosa mouse models, at post-natal day (PN) PN14 in rd1 mice; and at PN30 in rd2 and rd10 mice. Green bars represent the wild-type (wt) situation; red bars represent the untreated mutant situation. A) rd1 animals treated with free DF003 did not show any improvement on photoreceptor survival when compared to untreated rd1. In contrast, LP-DF003 treatment significantly preserved rd1 photoreceptors at PN14. B) At PN30 retinal degeneration in rd2 mice has caused the loss of approx. 15% of photoreceptors, while in rd10 retina at the same age around 80% are lost. In both rd2 and rd10 animals, treatment with LP-DF003 significantly increased the number of surviving photoreceptors.

To assess the effects of LP-DF003 in vivo, we used three different retinitis pigmentosa animal models carrying genetic defects homologous to human retinitis pigmentosa mutations. The rd1 mouse is an animal model for retinitis pigmentosa with a loss of function of the Pde6b gene, leading to a rapid cell death of rod photoreceptors until post-natal (PN) day 18 (Sanyal and Bal 1973, vide supra). At PN14 the rd1 retina has lost more than 50% of its photoreceptor rows, when compared to the wt (FIG. 2A). While systemic administration of DF003 via intraperitoneal injection (50 mg/kg once per day) had no effect on rd1 photoreceptor survival, treatment with LP-DF003 at the same concentration significantly increased rd1 photoreceptor viability.

The rd2 (rds) mouse is another model for retinitis pigmentosa carrying a mutation in the Prph2 gene that leads to a relatively slow loss of rod and cone photoreceptors in the first three post-natal months (Sanyal and Jansen 1981, vide supra). At PN30 about 15% of rd2 photoreceptors are lost. Already at this age rd2 animals treated with LP-DF003 (50 mg/kg every second day) exhibited a significant increase in the number of surviving photoreceptor rows (FIG. 2B).

The third animal model used was the rd10 mouse bearing a point mutation in the Pde6b gene. Here, degeneration is slower when compared to the rd1 mutant retina and the loss of rod photoreceptors starts at PN18 with around 80% lost at PN30. Also in rd10 animals, systemic administration of LP-DF003 via intraperitoneal injection (i.p.; 50 mg/kg once per day) significantly increased the survival of photoreceptors at PN30 (FIG. 2B). The same i.p. treatment of rd10 mice with control liposomes not containing DF003 ("empty" liposomes) did not yield any significant differences from untreated rd10 animals.

Figure 2B:
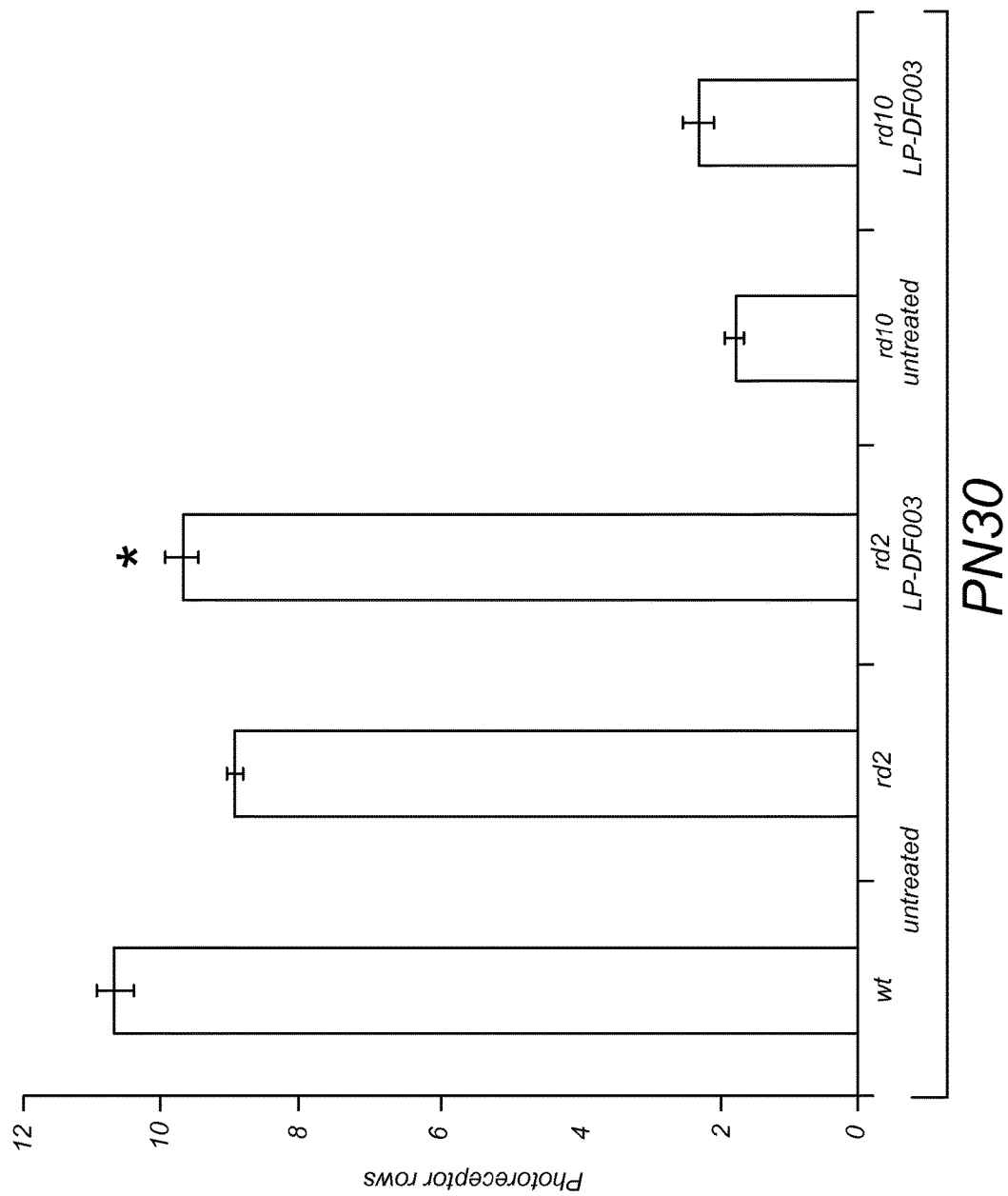
Figure 3A:
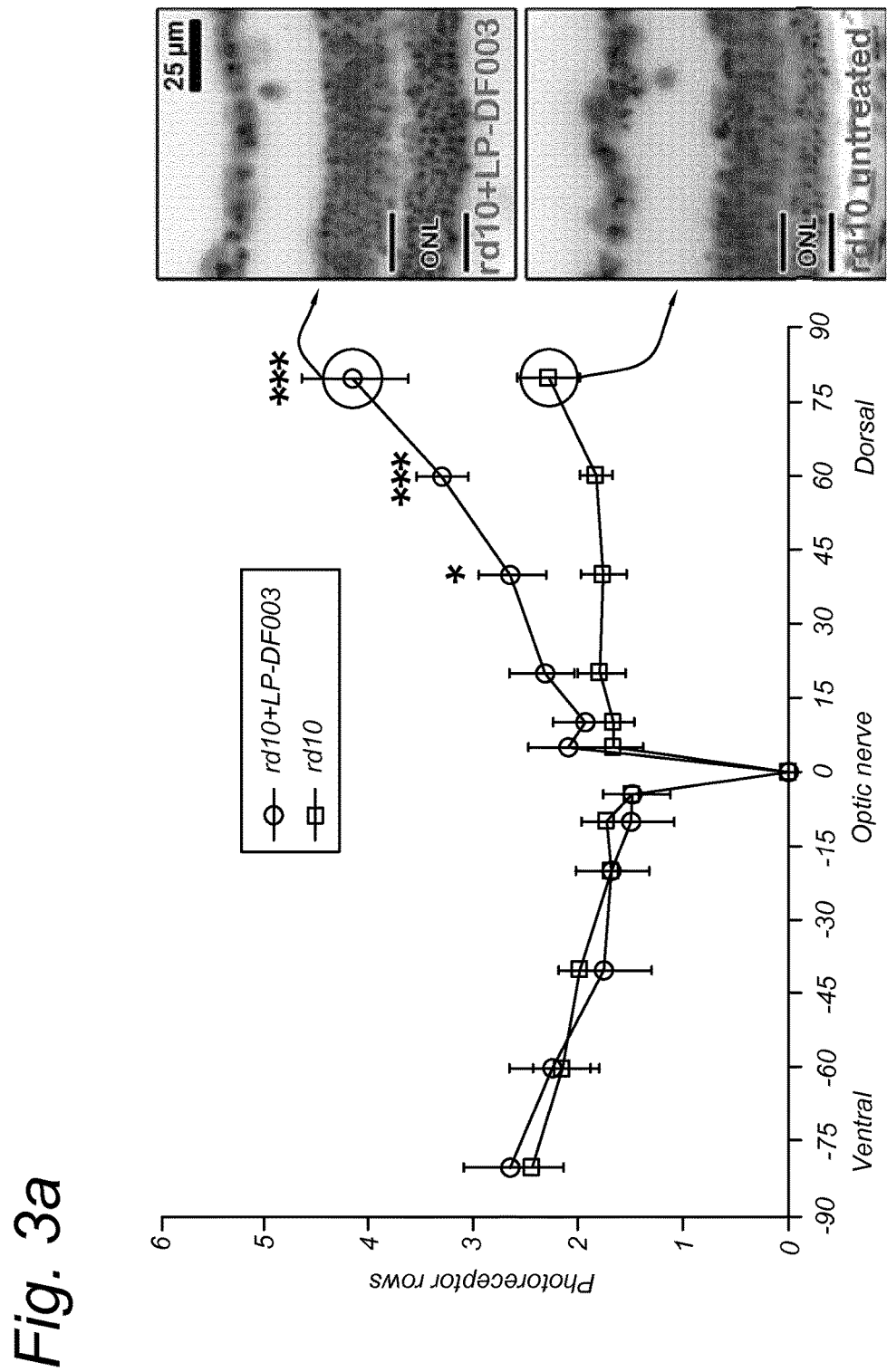
FIGS. 3A-3C. LP-DF003 preserves photoreceptor viability and function in rd10 animals in vivo. In mice, retinitis pigmentosa progresses from the centre (optic nerve=0°) to the periphery (90°). A) LP-DF003 rescued rd10 photoreceptors (ONL) in the dorsal parts of the peripheral retina, indicating slower disease progression. B) Representative electroretinographic (ERG) responses in untreated (red) and LP-DF003 treated (orange) rd10 animals. Adult wild-type traces (green) are shown for comparison. The bar graph shows that average (n=7) b-wave ERG amplitudes are 4-5 fold larger in treated rd10 animals.

The data shown in FIGS. 2A and 2B confirmed that overall photoreceptor survival was improved by LP-DF003 treatment. Since in rodent retinitis pigmentosa models the degeneration of photoreceptors progresses from the centre to the periphery, the protective effect was more pronounced in the periphery. This was assessed in so called Spider diagrams, which show the amount of surviving photoreceptors as a function of the eccentricity from the optic nerve, i.e. the centre of the retina. Thus, in the retinal periphery of LP-DF003 treated rd10 animals there were about two times more surviving photoreceptor than in untreated counterparts (FIG. 3A).

Figure 3B:
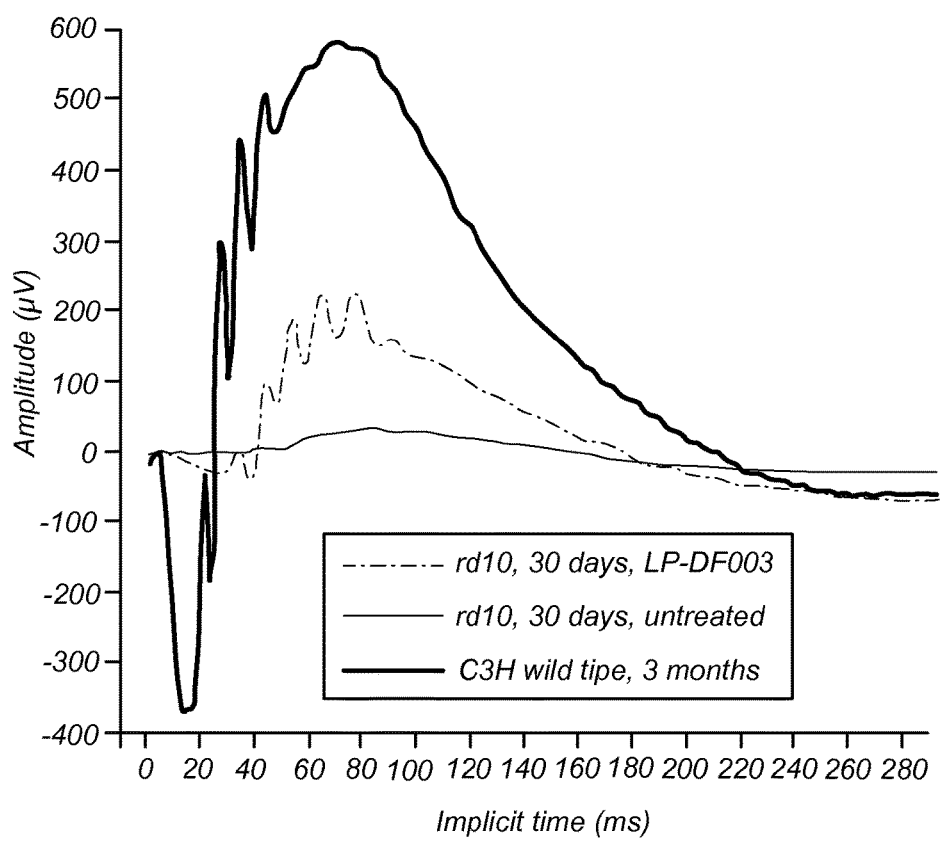
Figure 3C:
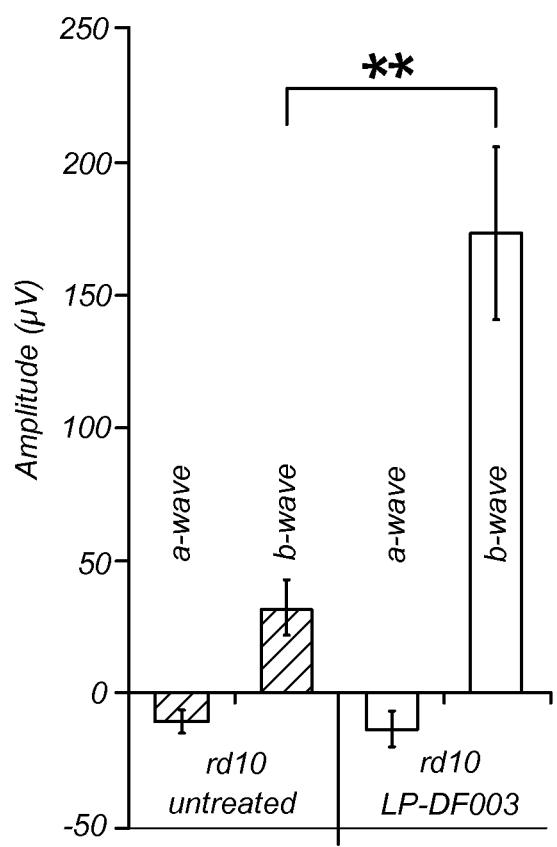

More importantly, i.p. LP-DF003 strongly improved the in vivo functionality of the retina as assessed by ERG recording in rd10 animals. In ERG the negative deflection of the electric response to light, the so called a-wave, reflects the primary response of the photoreceptors. The subsequent positive deflection, the so-called b-wave, corresponds to the response of the inner retina and the activation of second order neurons. While adult wt animals display ERG responses ranging from −350 µV (a-wave) to 600 µV (b-wave), the ERG of untreated rd10 animals is almost extinguished at PN30 (maximal b-wave response≈35 µV) (FIG. 3B). In contrast, i.p. LP-DF003 strongly and highly significantly improved rd10 ERG b-wave responses (≈180 µV), corresponding to a 4-5 fold improvement of retinal function.

Similar results were obtained when rd10 animal were treated with LP-DF003 via intravitreal injection (IVT). The injected eyes showed a strong increase in the numbers of surviving photoreceptor rows (treated: 4.66±0.45 SEM, contralateral: 1.57±0.17 SEM, n=8, p=0.0002). This was reflected by a corresponding increase in functional ERG responses, which at PN30 showed a highly significant increase to 250 µV in the treated eyes.

Overall the results of LP-DF003 treatment in the different retinitis pigmentosa animal models are highly encouraging and strongly highlight LP-DF003's potential for the development of a mutation-independent treatment for several different forms of human retinitis pigmentosa.

When the in vivo effects of Sp-8-Br-PET-cGMPS encapsulated into liposomes are compared to ordinary Sp-8-Br-PET-cGMPS, in the above animal models, a similar improvement in biological potential by encapsulation of Sp-8-Br-PET-cGMPS is observed as found for LP-DF003 compared to DF003.

2.2 Pharmacology

The active compound DF003 is an analogue of cGMP, blocking PKG activity with high specificity. This is particularly true for the PKG1α and PKG1β isoforms, while PKG2 is less well inhibited. The inhibitory constants for the two other potential targets CNGC and protein kinase A (PKA) isoforms 1 and 2 are 2-3 log units higher (Table 2) than those for PKG isoforms. cGMP and its analogues are targeting PKG and CNGC but could potentially also interfere with PKA, PDE or even HCN channel activity. The table gives the inhibitory constants ($K_i$) of DF003 for these targets and (where available) the $IC_{50}$ values.

TABLE 2

| | Inhibitory constants for DF003 | | | | | |
|---|---|---|---|---|---|---|
| Target | PKG1α | PKG1β | PKG2 | CNGC | PKA1 | PKA2 |
| $K_i$ | 0.035 μM | 0.03 μM | 0.45 μM | n.a. | >50 μM | 11 μM |
| $IC_{50}$ | | | 0.9 μM | 25 μM | | |
| Target | PDE1B | PDE2 | PDE4 | PDE5 | PDE10 | |
| $K_i$ | 2.5 μM | 0.8 μM | 8.1 μM | 4.1 μM | 5.0 μM | |

2.3 Pharmacokinetics

A pharmacokinetic study was performed in adult rats (3 months old) that received a single injection of either free DF003 or LP-DF003 at an initial dose of 20 mg/kg. Results are shown in FIG. 4. While the free DF003 was very rapidly cleared away from the blood-stream (estimated half-life: 10-15 min), high levels of DF003 remained within the blood stream when LP-DF003 was administered. Here, the estimated half-life was 24 h, corresponding to a 90 to 100-fold extension of half-life, approximately.

To ensure an optimal delivery of liposomes (e.g. containing DF003) to the retina, in both mice and rats a variety of application paradigms were tested for compounds encapsulated in the liposomal drug delivery system. These included topical application (eye drops), intravitreal injection into the eye, subtenon injection into the Tenon capsule surrounding the eye, intraperitoneal injection, and intravenous injection. The use of fluorescent tracer compounds within the liposomal delivery system made it possible to directly track compound delivery using scanning laser ophthalmoscopy (SLO; FIGS. 5A-5D). In mice and rats an intravenously applied fluorescent tracer (e.g. fluorescein) is otherwise cleared from the blood stream within a few hours.

Remarkably, direct applications to or into the eye resulted in no or almost no drug delivery to the retina, presumably due to the strong adhesion of the liposomes to non-retinal ocular structures (e.g. the vitreous). In contrast, systemic administration of liposomes by both intravenous and intraperitoneal injection resulted in a strong compound uptake in the retina, something that may be explained on the one hand by the prolonged circulation in the blood stream (cf. FIG. 4) and on the other hand by a facilitation of targeted transcytosis across the blood ocular barrier into the neuroretina. In mice, with liposomal formulation, the fluorescent tracer could be directly visualized in the retina via SLO for at least 4 days after a single intraperitoneal injection (FIGS. 5A-5D); in rats (not shown) the tracer was detectable for at least 10 days post injection.

2.4. Toxicology

Mice and rats treated with LP-DF003 (i.p.) for a duration of up to two months, as well as their untreated controls, were routinely examined in vivo and post mortem, without any macroscopic evidence for toxic drug effects.

Treated animals in vivo showed no alterations in behaviour (e.g. apathy, hunched, kyphotic posture), in the appearance of fur (e.g. hair loss, oily fur), or their skin (e.g. discolorations, haemorrhages). In vivo eye examinations found no abnormalities (e.g. lens opacity, cataract), while functional ERG testing revealed better performance in LP-DF003 treated animals, compared to untreated controls. Importantly, treated and untreated animals showed normal weight gains during their first two post-natal months and were generally undistinguishable from each other (data not shown). Likewise, macroscopic post mortem examination of internal organs (heart, liver, lungs, kidney, brain) revealed no abnormalities (organ size and form, coloration/perfusion) in LP-DF003 treated mice and rats. When mice were treated with the highest dose of LP-DF003 (200 μl i.p., every day), the spleen of some animals appeared bigger than in controls, a phenomenon that may be related to the administration of lipids. While this phenomenon did not seem to negatively affect the animals, it will be further evaluated and the lipid concentration in the drug formulation may be adapted accordingly.

Taken together and based upon these preliminary data, there is no evidence of any apparent and strong toxicological effects in these animals under the experimental conditions used. In particular, if in the human application an intravitreal injection is envisaged, the doses of LP-DF003 to be applied would be at least 400-1000 fold lower than what was used in the mouse and rat experiments.

The invention claimed is:

1. A pharmaceutically acceptable nanocontainer comprising an agent for treating or diagnosing a pathology, condition or disorder associated with dysregulation of a cGMP-effected cellular target,
    wherein the target is at least one of a cGMP-dependent protein kinase (PKG), a hyperpolarization-activated cyclic nucleotide-gated (HCN) channel, a phosphodiesterase (PDE) and a cGMP-gated channel (CNGC),
    wherein the agent is a cyclic guanosine-3', 5'-monophosphate analogue of the formula II:

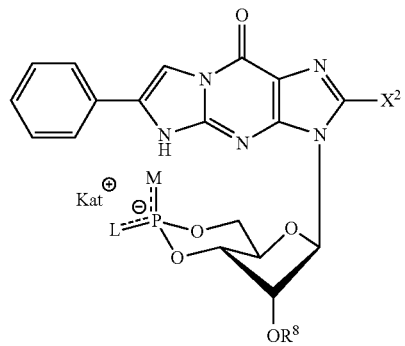

wherein
    $X^2$ is hydrogen, —F, —Cl, —Br, —I, CF3 or a —NR$^9$R$^{10}$ or —SR$^{11}$ group, wherein R9 is hydrogen and both R$^{10}$ and R$^{11}$ are alkyl groups with a terminal NH$_2$ or OH group,
    R$^8$ is hydrogen, a (tri)alkylsilyl group or an acyl group,
    L is oxygen, sulphur, borano (BH$_3$) or a further substituted borano group, and M is O(H), or
    L is O(H), and M is oxygen, sulphur, borano (BH$_3$) or a further substituted borano group,
    Kat$^+$ is Ca$^{2+}$, and
    wherein the agent is encapsulated into the nanocontainer by remote loading.

2. The nanocontainer according to claim 1, wherein the nanocontainer is conjugated to a ligand for a glutathione transporter.

3. The nanocontainer according to claim 2, wherein the cyclic guanosine-3', 5'-monophosphate analogue is the calcium salt of Rp-8-Br-PET-cGMPS.

4. The nanocontainer according to claim 2, wherein the ligand is selected from the group consisting of: glutathione, S-(p-bromobenzyl)glutathione, gamma-(L-gamma-azaglutamyl)-S-(p-bromobenzyl)-L-cysteinylglycin, S-butylglutathione, S-decylglutathione, glutathione reduced ethyl ester, glutathionesulfonic acid, S-hexylglutathione, S-lactoylglutathione, S-methylglutathione, S-(4-nitrobenzyl)glutathione, S-octylglutathione, S-propylglutathione, n-butanoyl gamma-glutamylcysteinylglycine, ethanoyl gamma-glutamylcysteinylglycine, hexanoyl gamma-glutamylcysteinylglycine, octanoyl gamma-glutamylcysteinylglycine, dodecanoyl gamma-glutamylcysteinylglycine, GSH monoisopropyl ester (N—(N-L-glutamyl-L-cysteinyl)glycine 1-isopropyl ester sulfate monohydrate) and glutathione derivatives of the formula V:

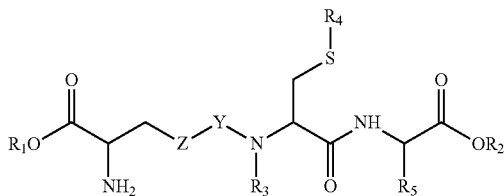

wherein $Z=CH_2$ and $Y=CH_2$, or $Z=O$ and $Y=C=O$;

$R_1$ and $R_2$ are independently selected from the group consisting of H, linear or branched alkyl (1-25C), aralkyl (6-26C), cycloalkyl (6-25C), heterocycles (6-20C), ethers or polyethers (3-25C), and where $R_1$-$R_2$ together have 2-20C atoms and form a macrocycle with the remainder of formula VI;

$R_3$ is selected from the group consisting of H and $CH_3$;

$R_4$ is selected form the group consisting of 6-8C alkyl, benzyl, naphthyl and a therapeutically active cyclic guanosine-3', 5'-monophosphorothioate; and, $R_5$ is selected from the group consisting of H, phenyl, $CH_3$- and $CH_2$-phenyl; or, a pharmaceutically acceptable salt thereof.

5. The nanocontainer according to claim 4, wherein $R_3$ is H, $R_4$ is benzyl, and $R_5$ is phenyl.

6. The nanocontainer according to claim 2, wherein the nanocontainer is a liposome encapsulating the therapeutic or diagnostic agent, and wherein the ligand for a glutathione transporter is conjugated to the liposome through a bifunctional conjugation agent comprising a vitamin E derivative or a phospholipid bonded to one end of the conjugation agent and the ligand for a glutathione transporter bonded to the other end of the conjugation agent.

7. The nanocontainer according to claim 6, wherein the conjugation agent is polyethylene glycol having polymerization number (n) of between 6-210.

8. The nanocontainer according to claim 7, wherein the polyethylene glycol has a molecular weight between 1,000 and 5,000 Da.

9. The nanocontainer according to claim 6, wherein the conjugation agent is obtainable by reacting distearoylphosphatidylethanolamine-polyethylene glycol-maleimide (DSPE-PEG-MAL) with a ligand for a glutathione receptor having a maleimide-reactive thiol group.

10. The nanocontainer according to claim 9, wherein the DSPE-PEG-MAL has a molecular weight of about 2,000 Da.

11. The nanocontainer according to claim 2, wherein the ligand for a glutathione transporter is glutathione.

12. A pharmaceutical composition comprising a nanocontainer according to claim 1 and pharmaceutically acceptable carrier.

13. A method of treating at least one of:
(a) retinitis pigmentosa or another a hereditary disease of the retina;
(b) secondary pigmentary retinal degeneration as a results of a metabolic or neurodegenerative disease, a syndrome or an eye disease;
(c) diseases of the retina comprising diabetic retinopathy, age related macular degeneration, macular Hole/Pucker, retinoblastoma, retinal detachment and river blindness,
the method comprising administering to a subject in need thereof a nanocontainer according to claim 1.

14. The method according to claim 13, wherein the nanocontainer is administered systemically or locally.

15. The method according to claim 14, wherein the nanocontainer is administered by at least one of
(a) injection or infusion by at least one of intravitreal, intravenous, intraperitoneal, and intraarterial routes; and
(b) topical or ocular application.

16. The method according to claim 13, wherein the nanocontainer is administered in doses of between 0.1 and 1000 mg/kg once per 1 or 2 days.

17. The method according to claim 13, wherein the nanocontainer is administered intravitreally in doses of between 0.0005 and 0.02 mg/kg once per two weeks or once per six weeks.

* * * * *